(12) United States Patent
Whitaker

(10) Patent No.: US 9,851,037 B2
(45) Date of Patent: Dec. 26, 2017

(54) FLUID CONNECTOR AND METHOD FOR MAKING SEALED FLUID CONNECTIONS

(71) Applicant: Nordson Corporation, Westlake, OH (US)

(72) Inventor: Carl T. Whitaker, Berthoud, CO (US)

(73) Assignee: Nordson Corporation, Westlake, OH (US)

( * ) Notice: Subject to any disclaimer, the term of this patent is extended or adjusted under 35 U.S.C. 154(b) by 0 days.

(21) Appl. No.: 14/819,570

(22) Filed: Aug. 6, 2015

(65) Prior Publication Data

US 2016/0053927 A1 Feb. 25, 2016

Related U.S. Application Data

(60) Provisional application No. 62/039,633, filed on Aug. 20, 2014.

(51) Int. Cl.
| | |
|---|---|
| *F16K 3/316* | (2006.01) |
| *F16L 29/00* | (2006.01) |
| *F16K 27/04* | (2006.01) |
| *F16K 3/00* | (2006.01) |
| *A61M 39/18* | (2006.01) |
| *A61M 39/22* | (2006.01) |

(52) U.S. Cl.
CPC ........... *F16L 29/007* (2013.01); *A61M 39/18* (2013.01); *F16K 3/00* (2013.01); *F16K 27/044* (2013.01); *A61M 2039/224* (2013.01)

(58) Field of Classification Search
CPC ....... F16L 29/007; F16L 29/00; F16K 27/044; F16K 27/041; F16K 3/00

USPC .... 137/614, 614.01; 251/326, 329, 107, 103
See application file for complete search history.

(56) References Cited

U.S. PATENT DOCUMENTS

| | | | | |
|---|---|---|---|---|
| 2,823,887 | A | | 2/1958 | Osinski |
| 2,828,146 | A | * | 3/1958 | Abbey ...................... F16K 3/02 |
| | | | | 137/614.01 |
| 4,223,868 | A | * | 9/1980 | Humes et al. .......... F16K 3/314 |
| | | | | 251/326 |
| 4,230,299 | A | * | 10/1980 | Pierce, Jr. ............... E21B 34/02 |
| | | | | 137/315.28 |

(Continued)

FOREIGN PATENT DOCUMENTS

| | | |
|---|---|---|
| AU | 2003256821 A1 | 2/2004 |
| CN | 200957243 Y | 10/2007 |

(Continued)

OTHER PUBLICATIONS

Colder Products Company, Aseptiquik® G Connector, Spec Sheet, SPEC1032 4/13 GLS 2000, 4 pgs.

(Continued)

*Primary Examiner* — Kevin Lee
(74) *Attorney, Agent, or Firm* — Baker & Hostetler LLP

(57) ABSTRACT

A connector adapted to form a fluid tight connection includes first and second housing sections defining a fluid path. A locking element is configured to selectively lock the first and second housing sections together. A slide seal is positioned generally between the first and second housing sections and is movable between a first, blocking position in which the slide seal blocks and seals the fluid path and a second, unblocking position in which the fluid path is unblocked.

31 Claims, 29 Drawing Sheets

(56) References Cited

U.S. PATENT DOCUMENTS

| | | | |
|---|---|---|---|
| 4,231,389 A * | 11/1980 | Still et al. | F16K 31/54 137/315.29 |
| 4,306,705 A | 12/1981 | Svensson | |
| 4,456,026 A | 6/1984 | Kantor | |
| 5,413,140 A | 5/1995 | Kimpel et al. | |
| 5,456,673 A | 10/1995 | Ziegler et al. | |
| 5,971,950 A | 10/1999 | Lopez et al. | |
| 6,116,278 A * | 9/2000 | Baumgardner et al. | F16K 3/0209 137/383 |
| 6,132,402 A | 10/2000 | Tessmann et al. | |
| 6,422,535 B1 * | 7/2002 | Stone et al. | F16K 3/0227 251/327 |
| 7,137,974 B2 * | 11/2006 | Almasian et al. | A61M 39/14 137/614 |
| 7,922,211 B2 | 4/2011 | Arthun et al. | |
| 8,491,016 B2 | 7/2013 | Williams et al. | |
| 9,027,968 B2 | 5/2015 | Gerst | |
| 2005/0045847 A1 * | 3/2005 | Powell | F16K 3/316 251/319 |
| 2013/0099489 A1 | 4/2013 | Williams et al. | |
| 2013/0207380 A1 | 8/2013 | Williams et al. | |
| 2013/0289517 A1 | 10/2013 | Williams et al. | |

FOREIGN PATENT DOCUMENTS

| | | |
|---|---|---|
| EP | 0943850 A1 | 9/1999 |
| FR | 2958365 A1 | 10/2011 |
| WO | 8001507 A1 | 7/1980 |
| WO | 2004011077 A1 | 2/2004 |
| WO | 2011125023 A1 | 10/2011 |
| WO | 2013123347 A1 | 8/2013 |
| WO | 2013162743 A1 | 10/2013 |

OTHER PUBLICATIONS

European Application No. 15180876.3: European Search Report dated Feb. 1, 2016, 8 pages.

* cited by examiner

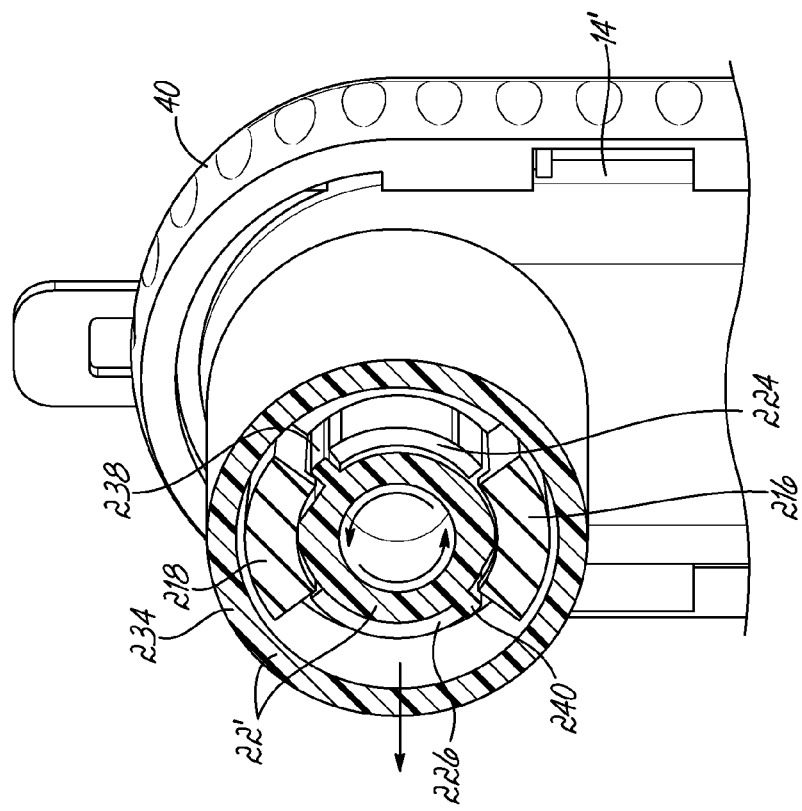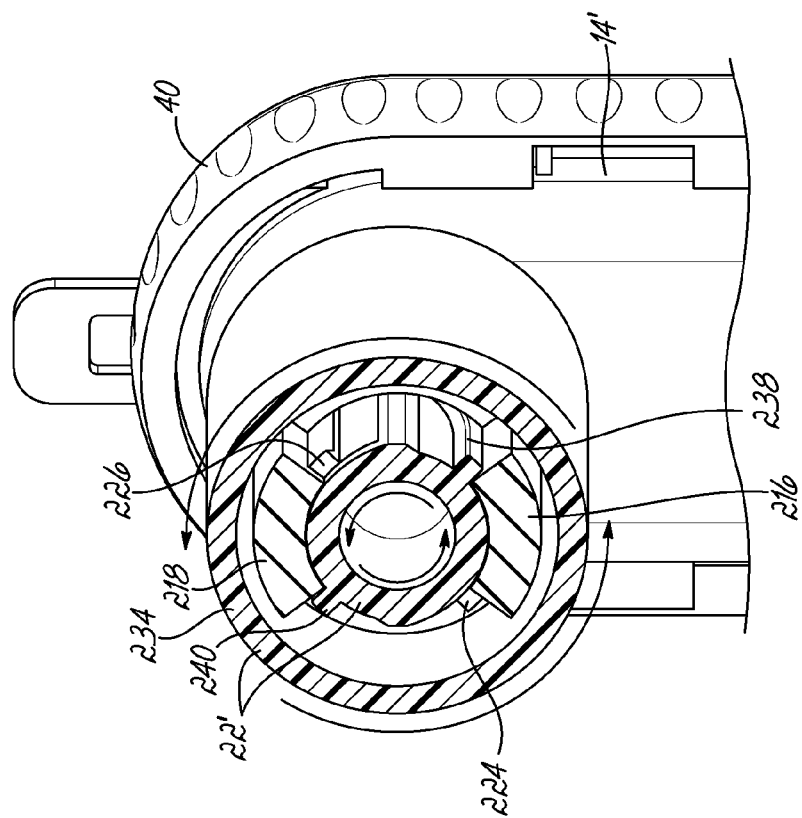

FLUID CONNECTOR AND METHOD FOR MAKING SEALED FLUID CONNECTIONS

CROSS-REFERENCE TO RELATED APPLICATION

This application claims the priority of Application Ser. No. 62/039,633 filed Aug. 20, 2014 (pending), the disclosure of which is hereby incorporated by reference herein.

TECHNICAL FIELD

The present invention generally relates to fluid connectors and methods for making fluid connections. More particularly, the invention relates to a connector and method for establishing a sterile connection in, for example, various industries including medical, biological, pharmaceutical, food and other industries.

BACKGROUND

In various industries, such as those mentioned above, it is often necessary to make repeated fluid connections while maintaining sterility at the connection site so as to prevent contaminants, such as dirt, dust or microorganisms from entering the fluid path at the connection site.

Various manners of maintaining sterility under such conditions have been developed in the past. These have included the use of steam or other sterilizing agents on the various fluid fittings or other components, including the connectors, so that sterile conditions are maintained throughout a process. If undertaken carefully, these methods can effectively maintain sterile conditions. However, such methods are time consuming and susceptible to human error. Therefore, especially in environments where productivity as well as robust sterilization procedures are necessary, these methods have given way to more efficient methods. In particular, disposable fluid connectors and fluid conduit systems are now in use and provide cost effective, efficient and yet robust manners of maintaining sterile conditions. For example, the disposable connector of U.S. Pat. No. 7,137,974 utilizes plug elements for maintaining the connector under sterile conditions. A slide member is used to move the plug elements from a position in which they block the fluid path to a position in the connector in which they do not block the fluid path. Once the plug elements are moved out of the blocking position, conduits may be moved together within the connector to make a fluid connection under sterile conditions.

It would be desirable to provide a fluid connector capable of making a fluid connection under sterile conditions, that is more easily manufactured and more efficiently used than past connectors.

SUMMARY

In a first illustrative embodiment, a connector is provided and forms a fluid tight connection, such as under sterile or aseptic conditions. The connector generally includes first and second housing sections defining a fluid path. A locking element is configured to selectively lock the first and second housing sections together. A slide seal is positioned generally between the first and second housing sections and moves between a first, blocking position in which the slide seal blocks and seals the fluid path and a second, unblocking position in which the fluid path is unblocked.

The first and second housing sections further include first and second fluid connector ports coupled respectively to the first and second housing sections. The first and second fluid connector ports are each adapted to fluidly couple with respective first and second tubular fluid connecting elements configured to direct fluid along the fluid path.

In an alternative embodiment, a first connector port is coupled to the first housing section, a first tubular fluid connector element is configured to selectively couple with the first connector port; and a second tubular fluid connecting element is integrally formed or otherwise rigidly fixed with the second housing section. The first and second tubular fluid connecting elements are operative to direct fluid along the fluid path.

The slide seal includes a sealing portion and a grasping end generally opposite the sealing portion. Preferably, the sealing portion carries a resilient sealing element which, for example, may be an overmolded rubber element. The grasping portion is adapted to be grasped by a user to move the slide seal generally through and in fluid tight sealing engagement with the housing sections during movement between the first, blocking position and the second, unblocking position. The first housing section includes a first sealing surface, and the second housing section includes a second sealing surface. Again, these sealing surfaces may be overmolded rubber elements. The first and second sealing surfaces engage each other in a fluid tight manner when the first and second housing sections are locked together with the locking element. The sealing portion of the slide seal further includes a sealing surface which contacts the first and second sealing surfaces of the housing sections when the first and second housing sections are locked together with the locking element and the slide seal is in the first, blocking position. The slide seal further comprises a vent for preventing vacuum from being formed in the fluid path as the slide seal is moved from the first, blocking position to the second, unblocking position.

The slide seal further comprises a distal sealing tip and a proximal sealing end, and a stop element is provided to stop the slide seal at the second, unblocking position such that distal sealing tip does not move to or past the location of the first and second sealing surfaces that is contacted by the proximal sealing end when the slide seal is in the second, unblocking position. This feature helps prevent contaminants from entering the fluid path from the outside environment.

The connector further includes a latch element on at least one of the first or second housing sections. The latch element selectively latches the slide seal in the first, blocking position and may also include the stop element for stopping the slide seal at the second, unblocking position.

A first generally tapered space is formed between the first and second sealing surfaces of the first and second housing sections when the first and second housing sections are positioned adjacent to each other in an unlocked condition. The slide seal is formed in first and second seal sections. A second generally tapered space is formed between the first and second seal sections when the first and second housing sections are positioned adjacent to each other in an unlocked condition. When the locking element is moved to lock the first and second housing sections together, the first and second generally tapered spaces are closed to thereby force fluid and/or air away from contacting locations between the first and second seal sections of the slide seal and away from the first and second sealing surfaces of the first and second housing sections. This helps prevent contaminants from entering the fluid path as the connection is made.

The slide seal sections are capable of being separately moved to the blocking position in the respective housing sections. In this manner, for example, the first and second housing sections may be in different locations and respectively coupled with the first and second slide seal sections. With the slide seal sections in their blocking positions, these assemblies (i.e., halves of the connector) may be sterilized in any suitable manner. More preferably, the slide seals are pulled back to their unblocking positions before sterilizing. This allows the sealing surfaces of the housing to be sterilized, for example, in an autoclave or by other means. Then, the connector halves may be coupled together in a manner as disclosed herein to form a sterile fluid connection and fluid path through the connector.

In another illustrative embodiment, a connector is provided for forming a fluid tight connection, such as under sterile or aseptic conditions, and generally includes first and second housing sections defining a fluid path. A locking collar is coupled to the first and second housing sections in a sliding manner, and slidably moves between an unlocked position in which the first and second housing sections are separable, and a locked position in which the first and second housing sections are locked together in engagement with the locking collar. A slide seal is positioned generally between the first and second housing sections and moves between a first, blocking position in which the slide seal blocks and seals the fluid path and a second, unblocking position in which the fluid path is unblocked.

The locking collar further comprises a U-shaped element having a closed end and an opposite, open end. The slide seal includes a sealing portion positioned adjacent the closed end of the U-shaped element when the slide seal is in the first, blocking position, and a grasping end generally opposite the sealing portion and adapted to be grasped by a user to move the slide seal generally through the open end of the U-shaped element during movement between the first, blocking position and the second, unblocking position.

Methods of making a fluid connection between first and second tubular fluid connector elements are also provided. One illustrative method includes blocking a fluid path at a location generally between the first and second housing sections by moving a first slide seal section to a blocking position in the first housing section and moving a second slide seal section to a blocking position in the second housing section. The first and second housing sections are locked together while the first and second slide seal sections are in their blocking positions to seal the fluid path. The slide seal sections are moved to an unblocking position. The first and second tubular fluid connector elements are then coupled together for fluid communication along the fluid path by moving at least one of the first or second tubular fluid connector elements with respect to the other along the fluid path.

Coupling the first and second tubular fluid connector elements further comprises directing the first and second tubular fluid connector elements respectively into first and second fluid connector ports of the respective first and second housing sections; and fluidly coupling the first and second tubular fluid connector elements to each other along the fluid path. In another alternative, coupling the first and second tubular fluid connector elements further comprises directing the first tubular fluid connector element into a first fluid connector port of the first housing section; and fluidly coupling the first tubular fluid connector element to a second tubular fluid connector element which is fixed to the second tubular housing section.

The method further includes sliding the first and second slide seal sections as a unitary slide seal generally through and in fluid tight sealing engagement with the housing sections during movement between the blocking position and the unblocking position. The first housing section includes a first sealing surface, and the second housing section includes a second sealing surface. Locking the first and second housing sections together further includes engaging the first and second sealing surfaces with each other in a fluid tight manner as the first and second housing sections are locked together. The first and second slide seal sections further include respective first and second sealing surfaces and the method further includes engaging the first and second sealing surfaces of the slide seal sections with the first and second sealing surfaces of the respective first and second housing sections when the first and second housing sections are locked together and the slide seal is in the blocking position.

The method further includes forming a first generally tapered space between the first and second sealing surfaces of the first and second housing sections and forming a second generally tapered space between the first and second seal sections of the slide seal. The first and second generally tapered spaces are closed as the first and second housing sections are locked together to thereby force fluid and/or air away from contacting locations between the first and second seal sections of the slide seal and the first and second sealing surfaces of the first and second housing sections.

The slide seal further comprises a distal sealing tip and a proximal sealing end, and the method further includes stopping the slide seal at the unblocking position using a stop element such that the sealing portion does not move to or past a location of the first and second sealing surfaces that may be contaminated when the slide seal is in the unblocking position.

As additional aspects, a latch element on at least one of the first or second housing sections selectively latches the slide seal in the blocking position, and the fluid path is vented through a vent path in the slide seal as the slide seal is moved to the unblocking position.

These and other features of the various embodiments of this invention will become more readily apparent to those of ordinary skill upon review of the following detailed description of the illustrated embodiments taken in conjunction with the accompanying drawings.

BRIEF DESCRIPTION OF THE DRAWINGS

FIG. 11A is a sectioned view of the movable tubular fluid connector element in a first position and initial rotation thereof to allow withdrawal of the movable tubular fluid connector element.

FIG. 11B is a sectioned perspective view similar to FIG. 11A, but illustrating the tubular fluid connector element rotated to a second position allowing withdrawal thereof.

DETAILED DESCRIPTION OF THE ILLUSTRATIVE EMBODIMENTS

Figure 1:
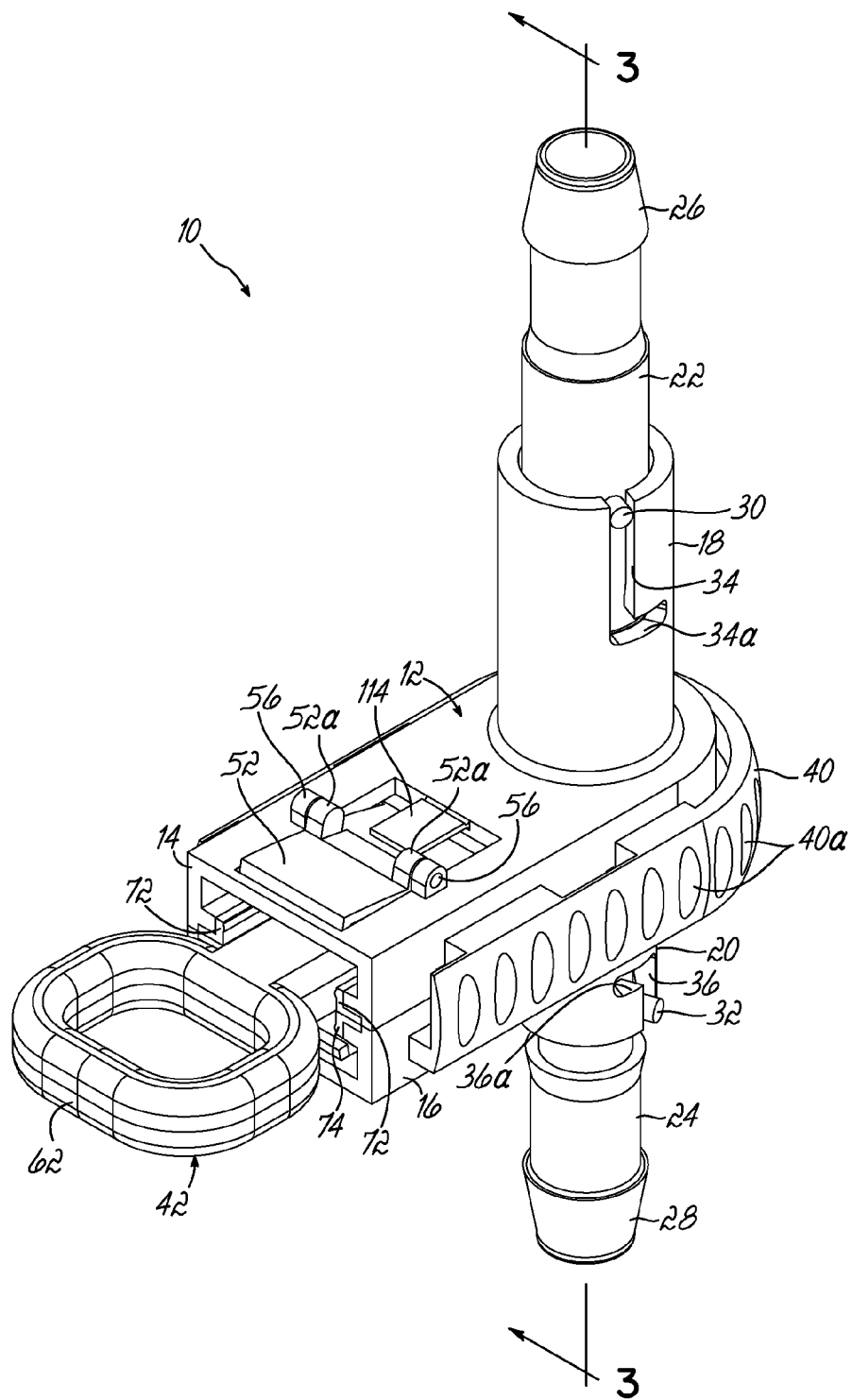
FIG. 1 is a perspective view illustrating a fluid connector constructed in accordance with a first embodiment.
Figure 2:
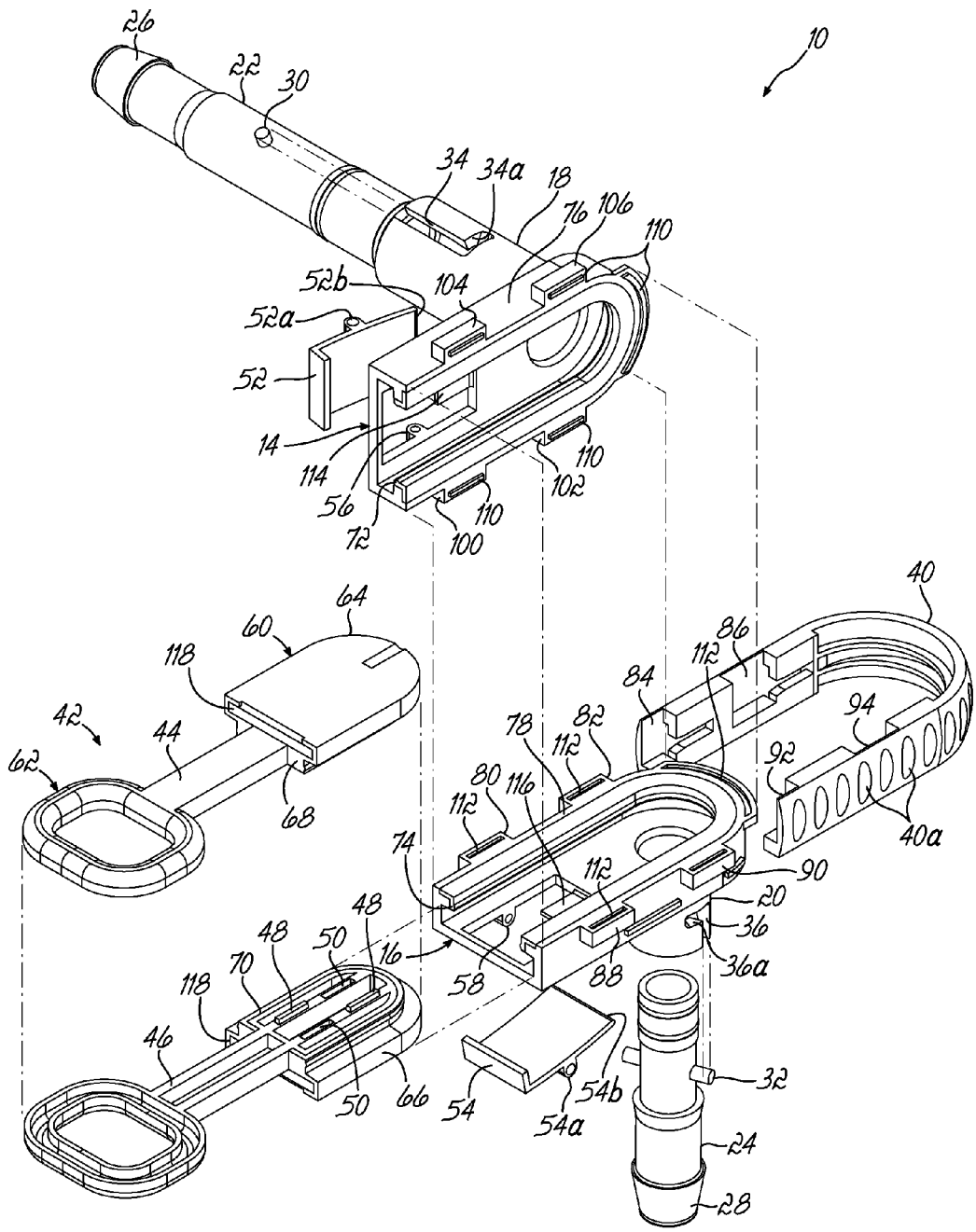
FIG. 2 is a disassembled perspective view of the fluid connector shown in FIG. 1.

Referring generally to FIGS. 1 and 2, a fluid connector 10 constructed in accordance with a first embodiment generally includes a housing 12 constructed of first and second housing sections 14, 16. Respective first and second integrally formed fluid connector ports 18, 20 extend from the first and second housing sections 14, 16 and receive respective first and second tubular fluid connector elements 22, 24. Ports 18, 20 and elements 22, 24 essentially define openings into the housing to establish fluid flow therethrough as will be described further below. The first and second tubular fluid connecting elements 22, 24 may include barbs 26, 28 at their outer ends for removably receiving flexible tubing, such as conventional silicone tubing (not shown). As will be further described below, the tubular fluid connecting elements 22, 24 can be releasably secured to the housing sections 14, 16. For example, the tubular fluid connector elements 22, 24 may include projections 30, 32 that are received in respective slots 34, 36 such that the tubular fluid connecting elements 22, 24 may be moved inwardly toward one another and then rotated and locked into place by rotating the respective projections 30, 32 into lateral or transverse portions 34a, 36a of the respective slots 34, 36.

The connector further includes a locking element 40 which is configured to selectively lock the first and second housing sections 14, 16 together. For example, the locking element 40 may be a U-shaped element having gripping indentations 40a along the outer periphery such that a user may grip and slide the locking element 40 between locked and unlocked positions as will be described below. A slide seal 42 is positioned within the housing 12 generally between the first and second housing sections 14, 16. The slide seal 42 is formed in first and second sections 44, 46 that may snap fit together with respective male connectors 48 and mating female connectors 50 (FIG. 2). As further shown in FIG. 2, a pair of latch elements 52, 54 are used to selectively latch the slide seal 42 in place in the position shown in FIG. 1. The latch elements 52, 54 include respective pivots 52a, 54a that couple with pivots 56, 58 on the housing sections 14, 16 to allow pivoting latching and unlatching movement described herein.

Figure 3:
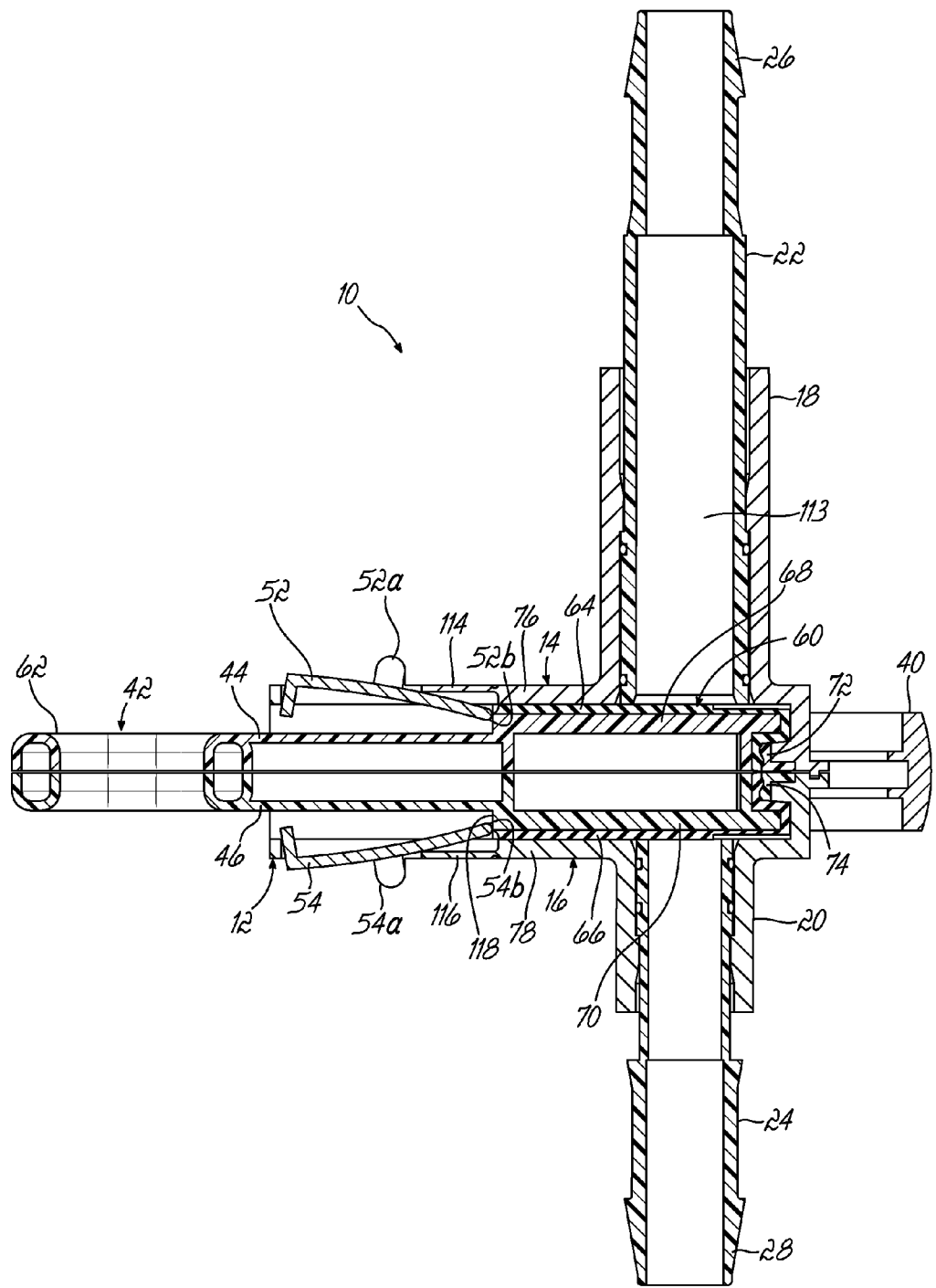
FIG. 3 is a cross sectional view taken along line 3-3 of FIG. 1.

Referring more specifically to FIGS. 2 and 3, the slide seal 42 includes a sealing portion 60 and grasping end 62 generally opposite the sealing portion 60. The sealing portion 60 comprises respective overmolded rubber elements 64, 66 on rigid plastic structural base elements 68, 70 of the slide seal 42. A user may grasp the grasping end 62 to move the slide seal 42 generally through and in fluid tight sealing engagement with the housing 12. The first housing section 14 includes a first sealing surface 72, and the second housing section 16 includes a second sealing surface 74. Similar to the construction of the slide seal sections 44, 46, the housing sections 14, 16 each comprise a rigid plastic structural base element 76, 78 and the first and second sealing surfaces 72, 74 comprise overmolded elastomeric or rubber elements. Any of the various sealing surfaces described herein may be formed of a suitable sealing material such as elastomeric material. The first and second sealing surfaces 72, 74 engage each other in a fluid tight manner when the first and second housing sections 14, 16 are locked together with the locking element 40. As understood from FIG. 2, the second housing section 16 is placed within the U-shaped locking element 40 such that first and second tabs 80, 82 are received in first and second recesses 84, 86 of the locking element 40 and third and fourth tabs 88, 90 are located in third and fourth recesses 92, 94 of the locking element 40. Then the first housing section 14 is placed in facing, mating engagement with the second housing section 16. The first housing section also has respective pairs of tabs 100, 102 and 104, 106 that are received in the recesses 84, 86 and 92, 94, respectively. External, male projecting elements 110 are received within internal, female slots 112. The facing engagement is shown in FIG. 3. The slide seal sections 44, 46 are respectively and individually pushed into the sections 14, 16 of the housing 12 prior to the housing sections 14, 16 being brought together into facing engagement. In this manner, the rubber sealing elements 64, 66 of the seal sections 44, 46 respectively contact and seal against the first and second sealing surfaces 72, 74 of the respective housing sections 14, 16. The seal sections 44, 46 are moved to their respective blocking positions before the first and second housing sections 14, 16 are in adjacent, facing engagement as described above and shown in FIG. 3. Therefore, when the housing sections 14, 16 are brought together and locked, the slide seal 42 is formed as a unitary structure as the slide seal sections 44, 46 couple together by the engagement of snap connectors 48, 50. This results in the slide seal 42 being formed and initially positioned in the blocking position as shown in FIG. 3. Preferably, for purposes of using the connector 10 in a sterile fluid system, the separate assemblies 14, 44 and 16, 46 are sterilized such as by the use of gamma ray sterilization or steam. This may be done while the separate assemblies 14, 44 and 16, 46 are in different locations as long as the slide seal sections 44, 46 are in their blocking positions and maintained in those positions until the connection process is completed as described herein. More preferably, the assemblies 14, 44 and 16, 46 may be separately sterilized by first pulling back the respective slide seals 44, 46 to their unblocking positions. This allows the sealing surfaces 72, 74 and other housing structure to be sterilized before moving the slide seals to their blocking positions. The blocking position blocks a fluid path 113 (FIG. 3) between the first and second tubular fluid connecting elements 22, 24. When the slide seal 42 is in the blocking position shown in FIG. 3, the latch elements 52, 54 spring downward by way of bias created by stop elements 114, 116 such that front edges 52b, 54b of the latch elements 52, 54 are biased downward and against the rear or proximal surface 118 of the sealing portion 60. This maintains the slide seal 42 in the blocking position as shown in FIG. 3.

Figure 4:
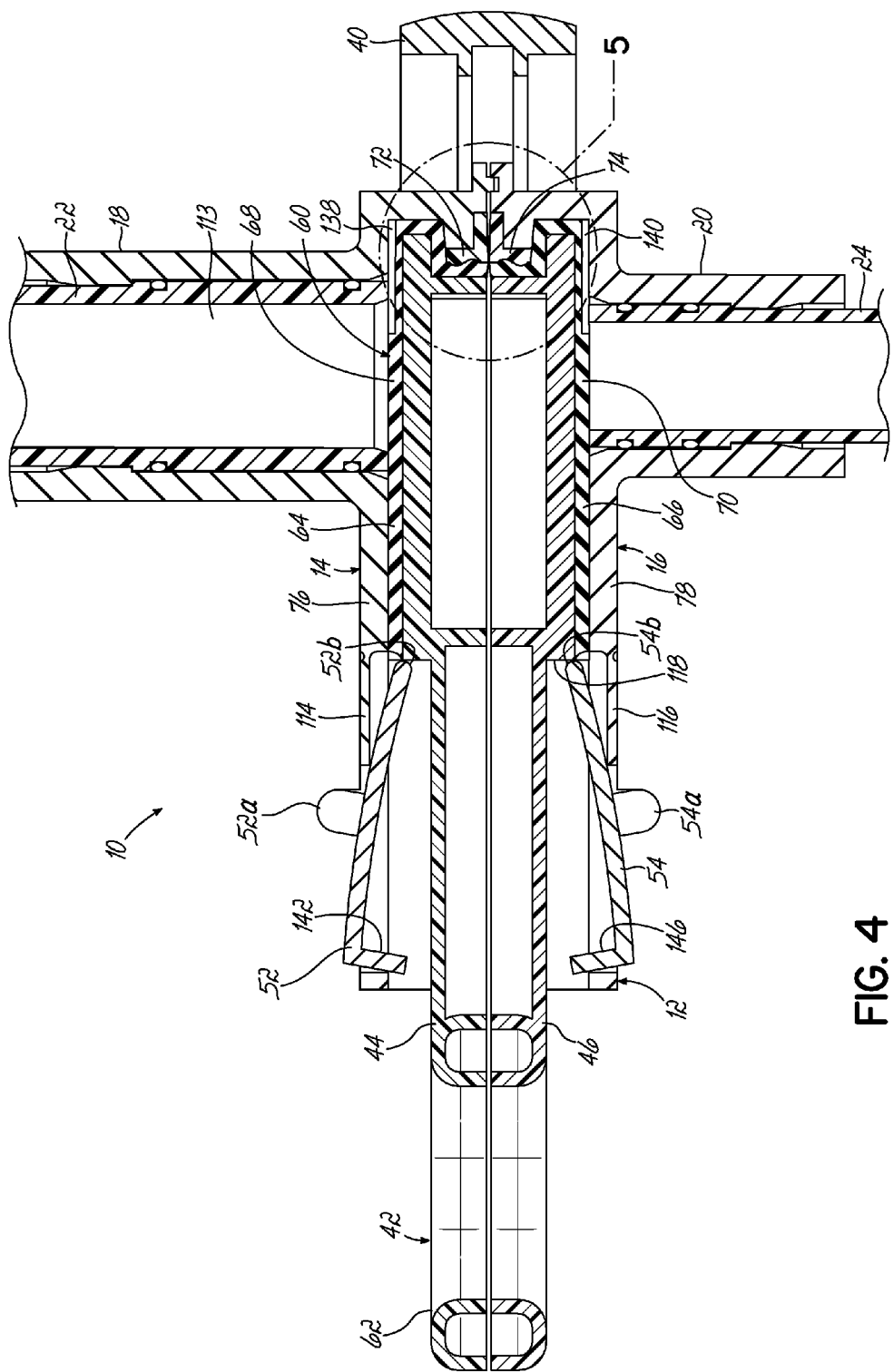
FIG. 4 is an enlarged portion of the cross sectional view shown in FIG. 3.
Figure 5:
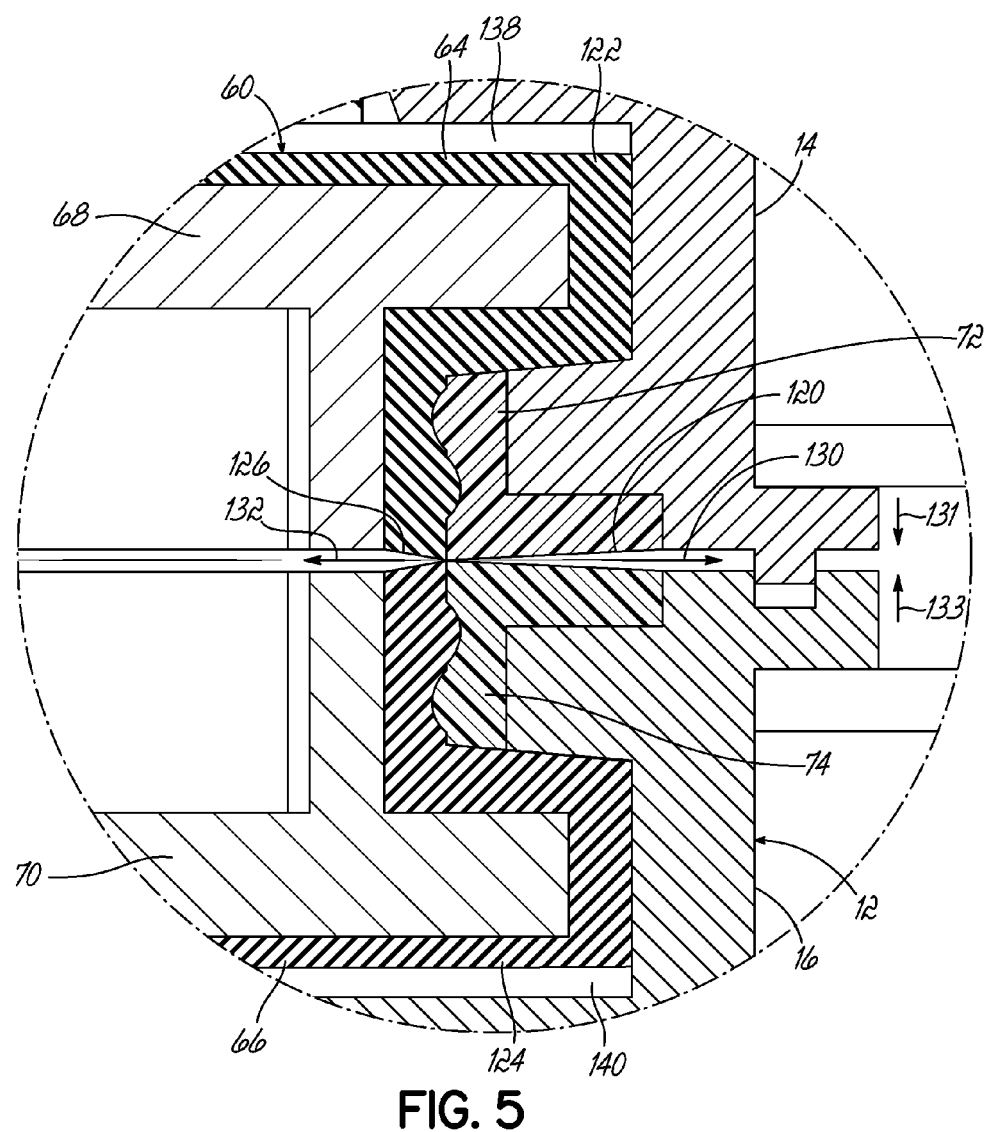
FIG. 5 is an enlarged view of encircled portion "5" shown in FIG. 4.

Referring to FIGS. 4 and 5, a first tapered space 120 (FIG. 5) is formed around the U-shaped perimeter and between the first and second sealing surfaces 72, 74 of the first and second housing sections 14, 16 when the first and second housing sections 14, 16 are positioned adjacent to each other in an unlocked condition. The sealing portion 60 of the slide seal 42 is formed in first and second seal sections 122, 124. A second tapered space 126 (FIG. 5) is formed around the U-shaped perimeter and between the first and second seal sections 122, 124 of the slide seal 42 when the first and second housing sections 14, 16 are positioned adjacent to each other in an unlocked condition as shown in FIG. 4. It will be appreciated that the tapered spaces 120, 126 may have other more generally tapered shapes, which operate to keep contaminants away from sealed portions of the connector 10.

Figure 6A:
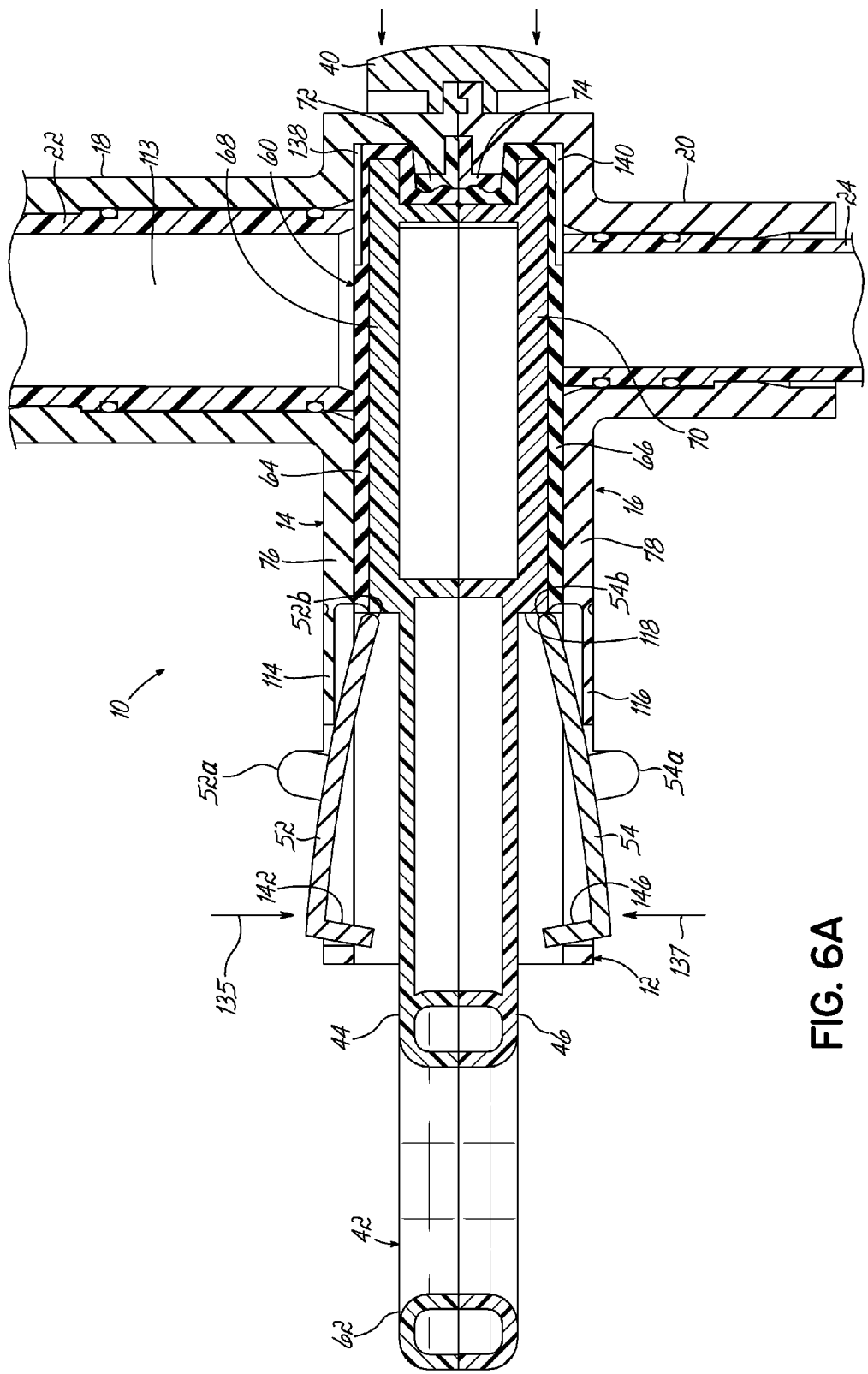
FIG. 6A is a cross sectional view similar to FIG. 4, but illustrating the locking collar moved into the locked position with the slide seal in the blocking position.
Figure 6B:
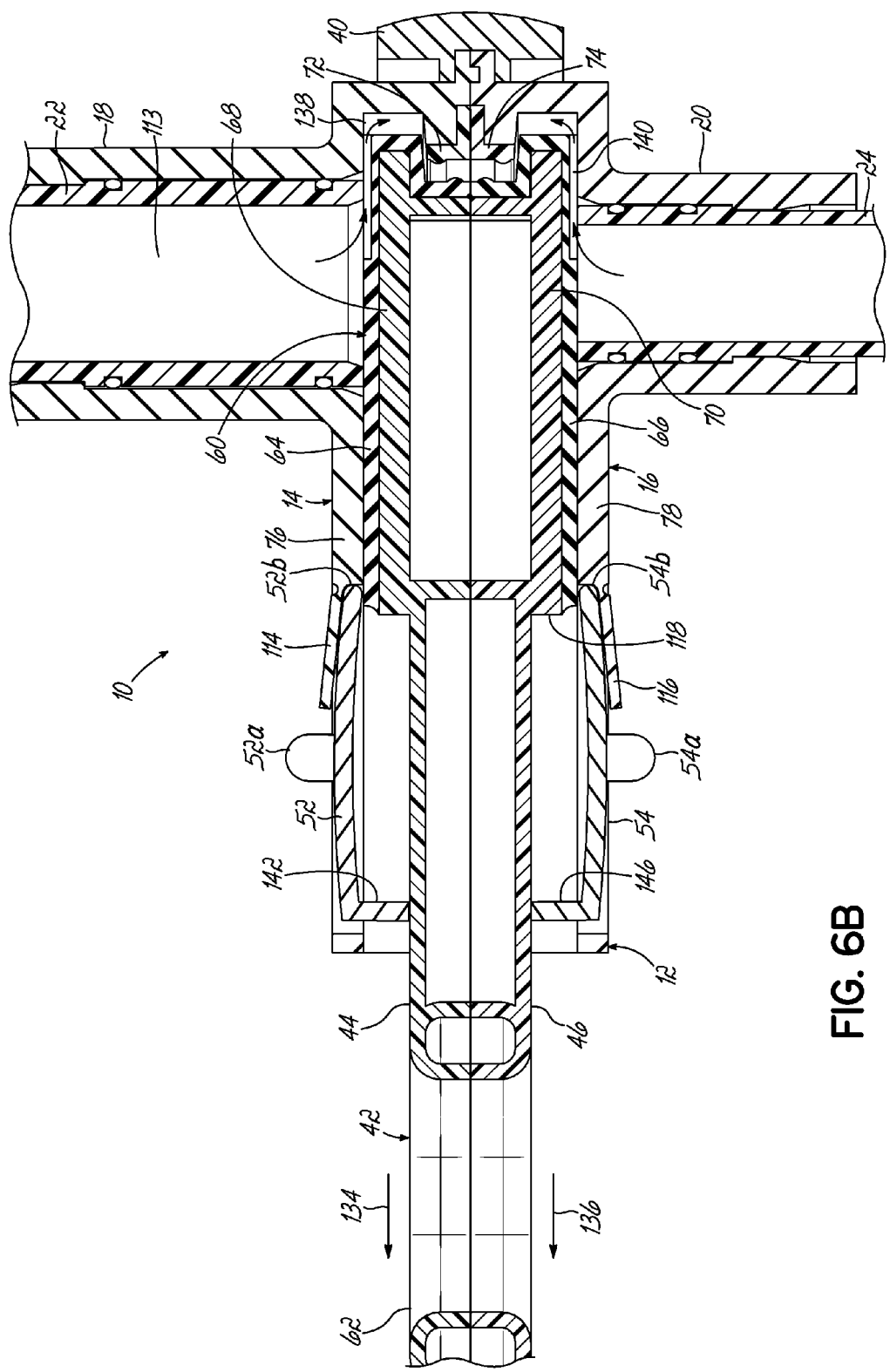
FIG. 6B is a cross sectional view similar to FIG. 6A, but illustrating the slide seal during its initial outward movement toward the unblocking position.
Figure 6C:
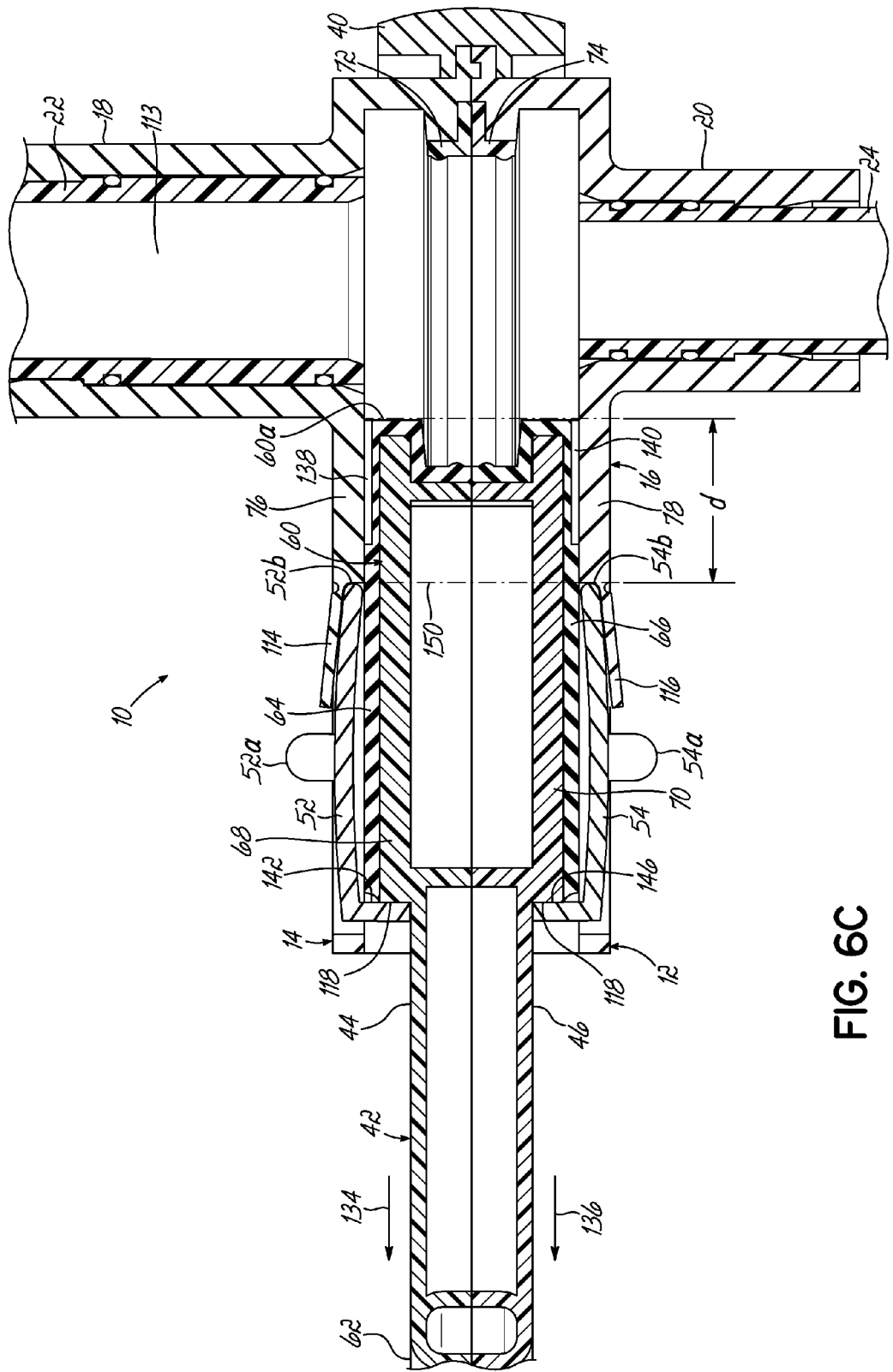
FIG. 6C is a cross sectional view similar to FIG. 6B, but illustrating the slide seal in the unblocking position.
Figure 6D:
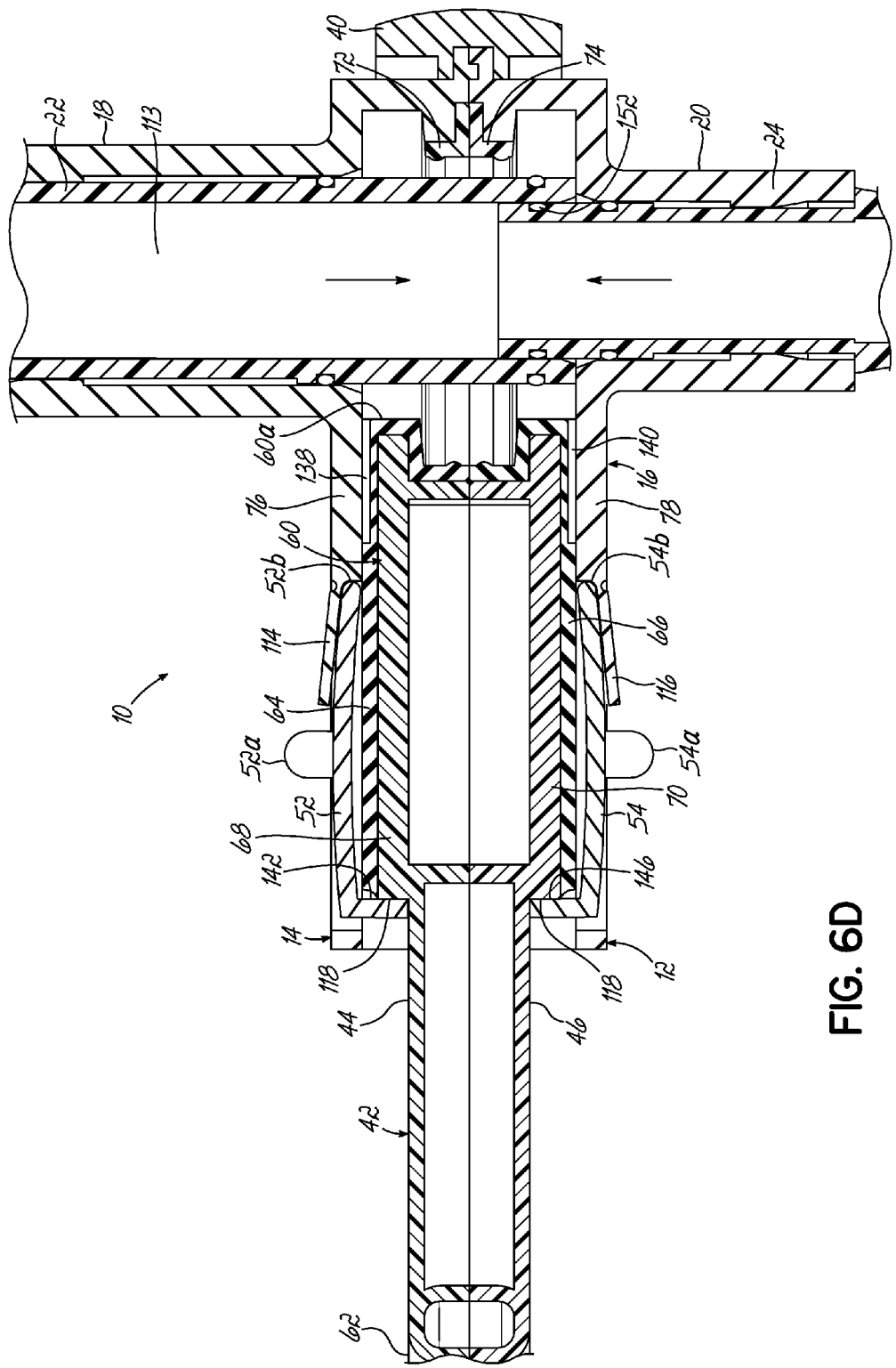
FIG. 6D is a cross sectional view similar to FIG. 6C, and further illustrating movement of the tubular fluid connector elements into engagement with each other to establish a fluid path therein.

As illustrated in FIG. 6A, when the locking element 40 is moved into a locked position this forces the two housing sections 14, 16 together and simultaneously forces the two seal sections 122, 124 together with a clamping action. As schematically illustrated in FIG. 5 with arrows 130, 132, this effectively squeezes or pushes air and/or fluid outward away from the sealing surfaces 72, 74 and seal sections 122, 124 and closes the tapered spaces 120, 126 as indicated by the arrows 131, 133. Therefore, air and/or fluid being squeezed outward in opposite directions will be directed toward the outside of the connector housing 12 (that is, in the direction of arrow 130), or will be directed into the space between structural base elements 68, 70 of the slide seal 42 (that is, in the direction of arrow 130). This prevents any contaminants from moving in the directions opposite to arrows 130, 132, i.e., into the sealed area of the connector 10 and into the fluid path 113 (FIG. 4). The slide seal 42 may be grasped at the end 62 and after the latch elements 52, 54 have been squeezed together as shown in FIG. 6A (see arrows 135, 137) to raise the distal tips 52b, 54b out of the way and against the stop elements 114, 116, the slide seal 42 may be pulled outward in the direction of the arrows 134, 136 as shown in FIG. 6B. Respective vent channels 138, 140 are formed in the sealing portion 60 to allow sterile gas, for example, to enter the space in the fluid path 113 being created by the outwardly moving slide seal 42. This prevents a significant vacuum effect from inhibiting movement of the slide seal 42 in the outward direction. The slide seal 42 is moved completely to the unblocking position shown in FIG. 6C and is stopped by engagement of rear or proximal surface 118 against rear surfaces 142, 146 of the latch elements 52, 54. These surfaces 142, 146 serve as stop elements stopping the slide seal 42 at the second, unblocking position such that the sealing portion 60 does not move to or past the location 150 of the first and second sealing surfaces 72, 74 that is contacted by a corresponding area of the sealing portion 60 when the slide seal 42 is in the second, unblocking position. The connector design ensures this by stopping the slide seal 42 distal tip 60a a distance "d" from that location 150. This prevents contaminants from entering the fluid path 113. Finally as shown in FIG. 6D, the tubular fluid connecting elements 22, 24 are pushed inwardly toward one another and are sealed to each other and to the connector ports 18, 20 via O-rings 152. The first and second tubular fluid connector elements 22, 24 are then rotated into locked positions using the projections 30, 32 and slots 34, 36 as described in connection with FIG. 1.

FIGS. 7 through 11D illustrate another embodiment of a fluid connector 10' constructed in accordance with various principles of the invention. In these figures, like reference numerals refer to like elements of structure with the first embodiment, described above. Therefore, these like elements will be understood to have the functions and features as discussed above and further description herein is not generally necessary. Instead, the differences between this second embodiment and the first embodiment will be described in more detail below. Like reference numerals having prime ('), double prime (") or triple prime ('") marks will be understood as referring to corresponding structure of the first embodiment but having slight design differences that will be described herein and/or understood from a review of the drawings. Unless described otherwise, such elements have the same function as described for the first embodiment. Aside from the described and/or illustrated differences, the structure, function and operation of the fluid connector is as described above in connection with the first embodiment.

Figure 7:
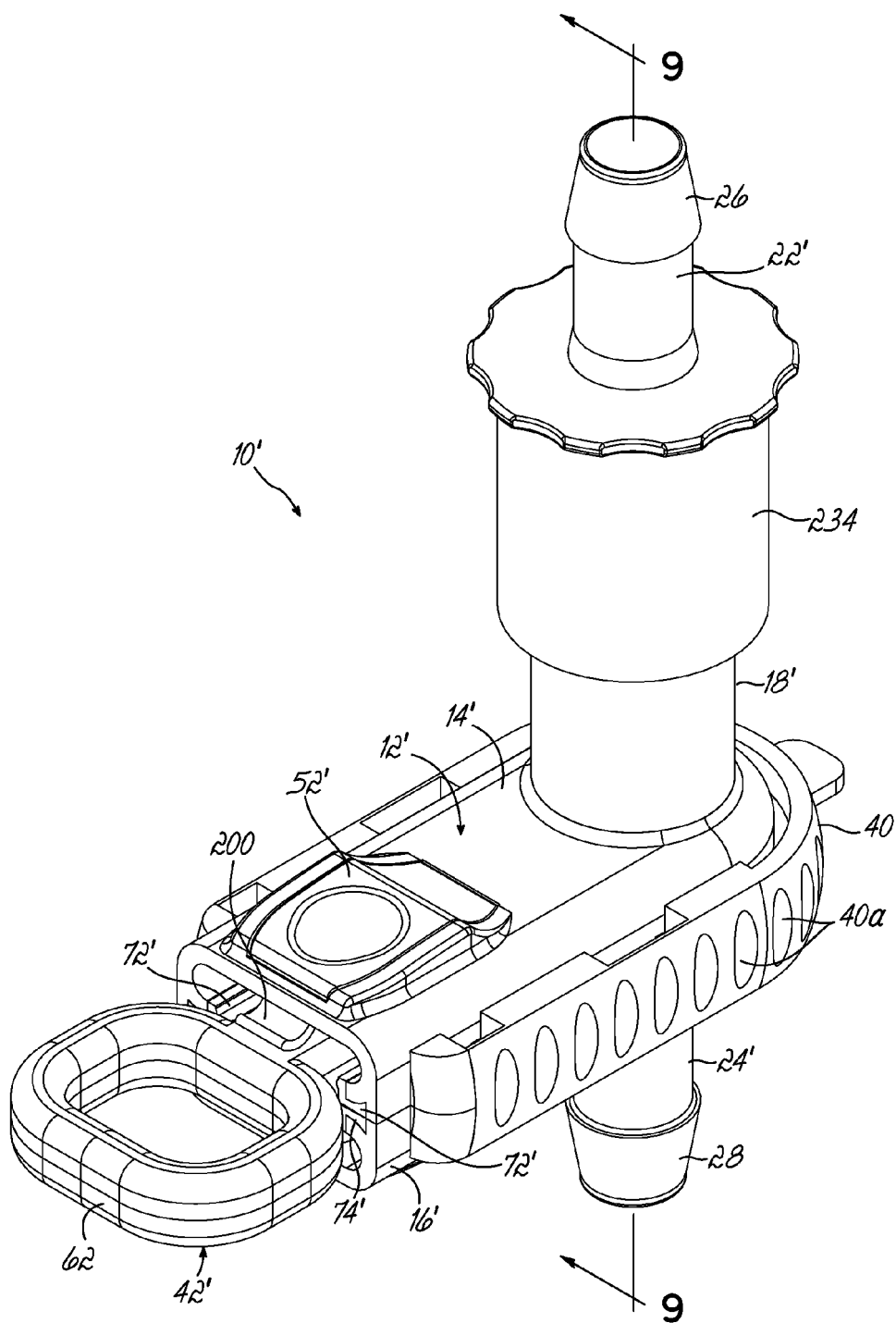
FIG. 7 is a perspective view of a fluid connector constructed in accordance with a second embodiment of the invention.
Figure 8:
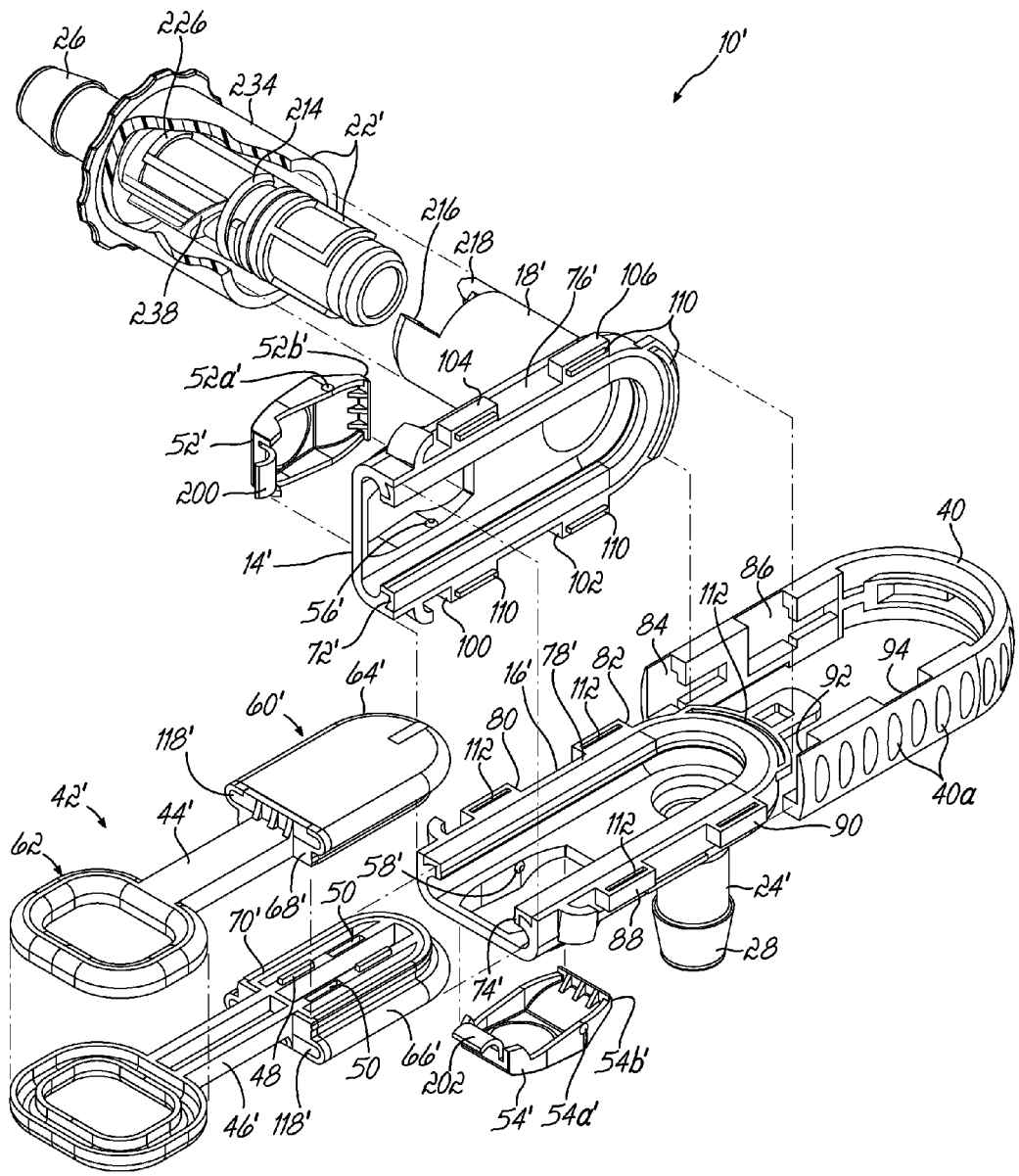
FIG. 8 is a disassembled perspective view of the fluid connector shown in FIG. 7.

Generally referring to FIGS. 7 and 8, the second tubular fluid connector element 24' is shown as integrally formed or otherwise rigidly fixed to second housing section 16'. Elements 18', 22' and 24' essentially define openings into the housing 12' to establish a flow path 113. The first tubular fluid connector element 22' is movable but has a different design and configuration than the first tubular fluid connector element 22 shown and described with respect to the first embodiment. These differences, described further below, simplify the construction and use of the fluid connector 10'. Additionally, the latch elements 52', 54' have a different design than the first embodiment and include integrally formed resilient spring or biasing elements 200, 202 allowing the latch elements 52', 54' to be moved between normally latched positions and, when squeezed together (FIG. 10B), unlatched positions allowing the slide seal 42' to be moved outward to its unblocking position. The slide seal 42' itself is generally of the same construction as previously described with regard to the first embodiment, except that the sealing portion 60' and its overmolded rubber sealing elements 64', 66' have a rounded peripheries for sliding within complementary rounded grooves or recesses comprising the sealing surfaces 72', 74' within the respective housing sections 14', 16'.

Figure 9:
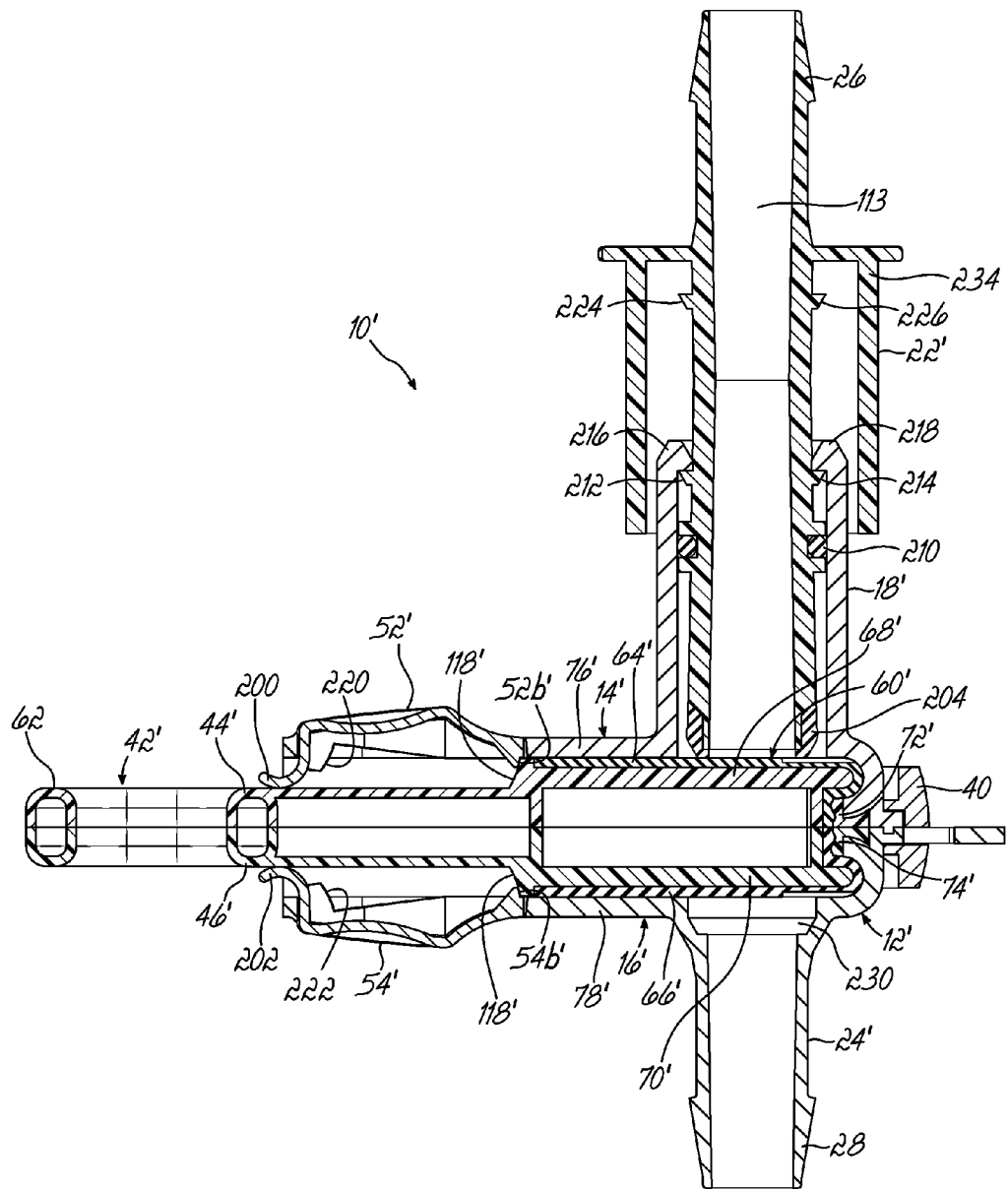
FIG. 9 is a cross sectional view taken along line 9-9 of FIG. 7.

FIG. 9 illustrates the fluid connector 10' in its closed state with the slide seal 42' blocking the fluid path 113 in a first position. In addition, the first tubular fluid connector element 22' is shown in a first position having its distal end 204 engaged with one side of the sealing portion 60' of the slide seal 42'. The locking element 40 is in its locked position and, therefore, the first and second housing sections 14', 16', are clamped together against the sealing portion 60' of the slide seal 42' maintaining sterile conditions within the connector 10' as previously described. The latch elements 52', 54' are in their normally latched positions with forward ends 52b', 54b' of each latch element 52', 54' engaged against a rear surface 118' of the sealing portion 60' to maintain the slide seal 42' in its blocking position. An O-ring 210 maintains a seal between the first tubular fluid connector element 22' and an upstanding first fluid connector port 18'. The first tubular fluid connector element 22' is maintained in the position shown by stop elements 212, 214 that engage underneath lips 216, 218 of the connector port 18' preventing outward movement of the first tubular fluid connector element 22'.

Figure 10A:
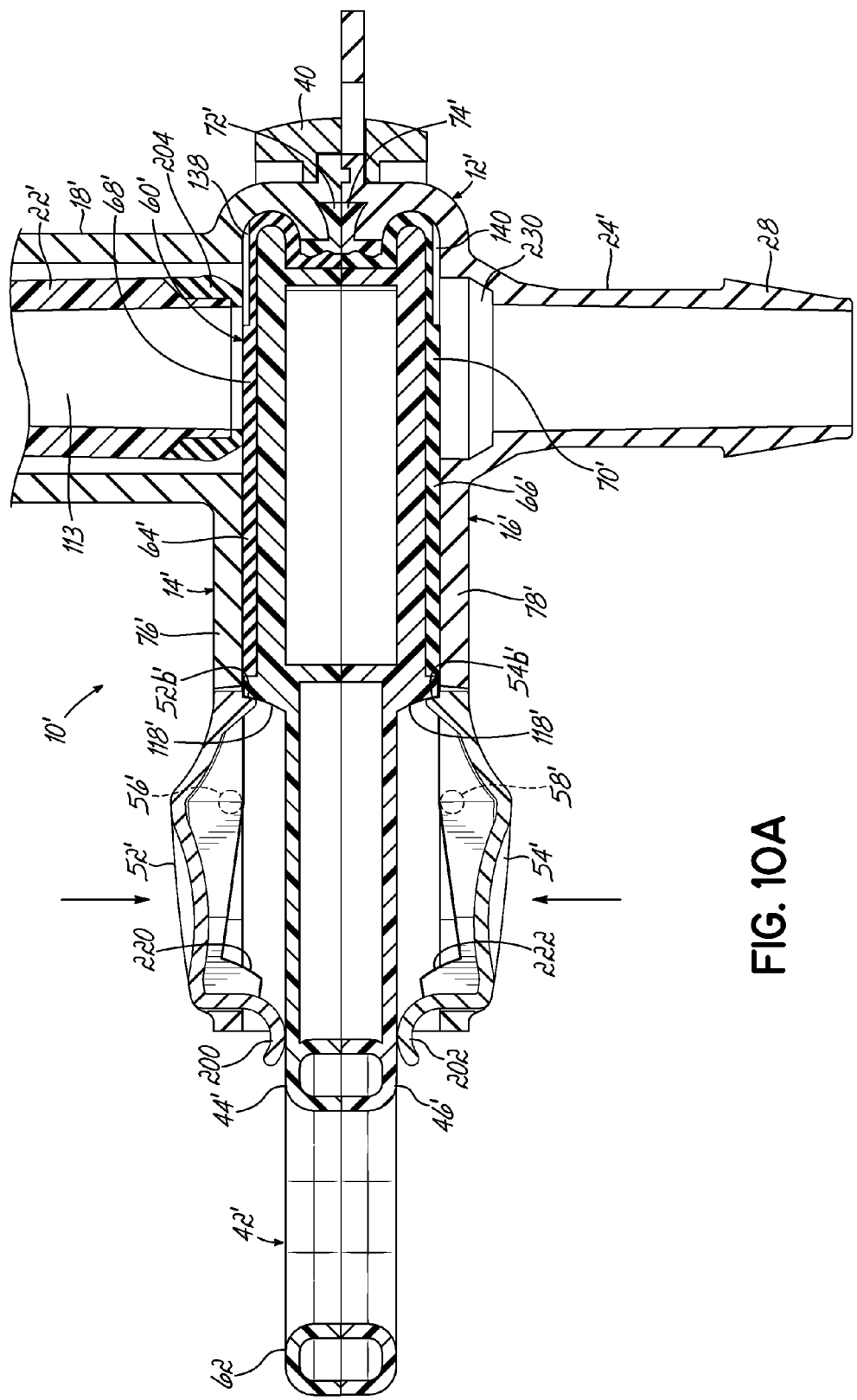
FIG. 10A is an enlarged portion of the cross sectional view shown in FIG. 9.
Figure 10B:
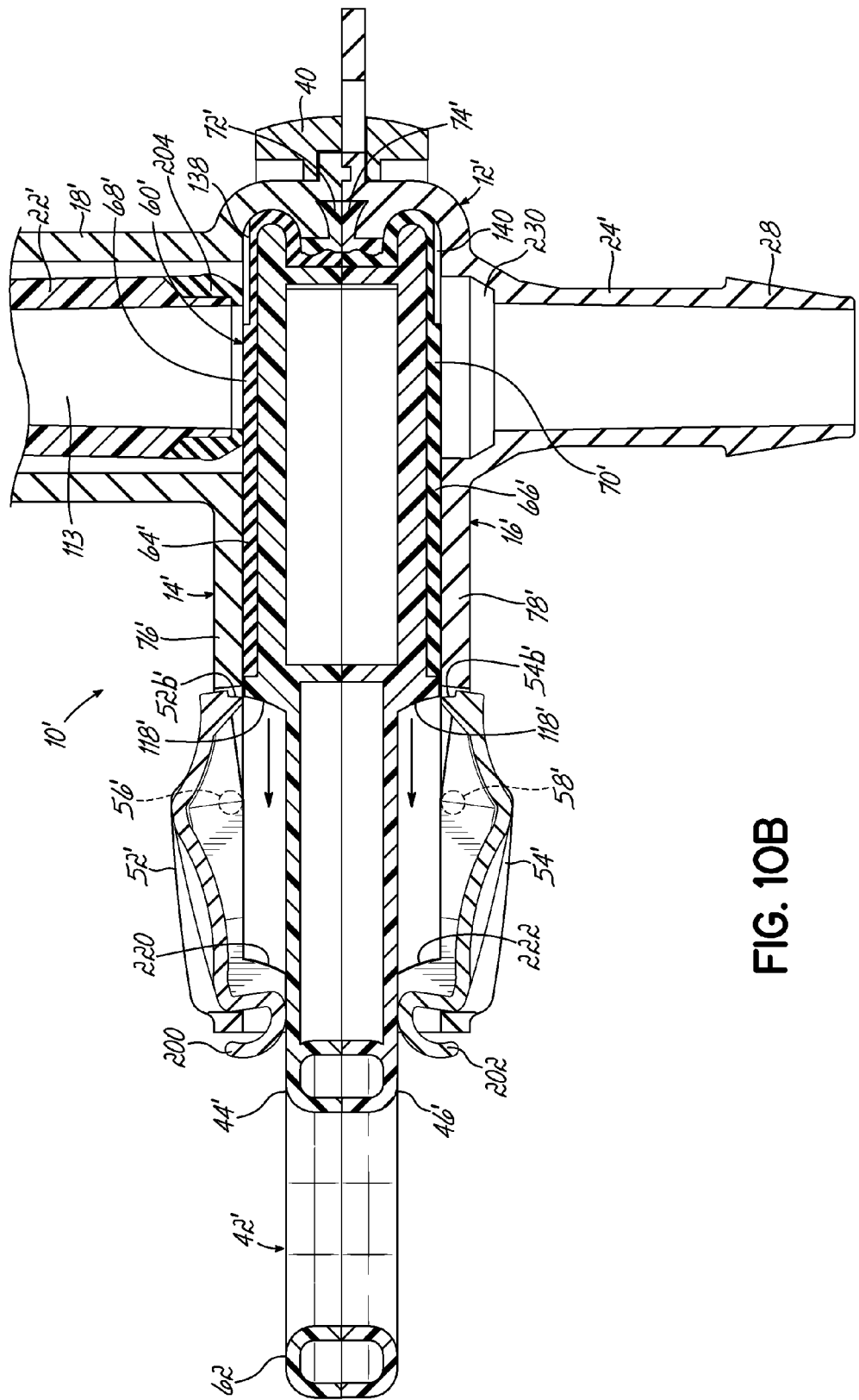
FIG. 10B is a cross sectional view similar to FIG. 10A, but illustrating the latching elements being unlatched so that the slide seal may be moved outward to its unblocking position.

FIG. 10A illustrates a first step of depressing the latch elements 52', 54' together. Specifically, a user holds the fluid connector 10' and depresses the latch elements 52', 54' together by squeezing the latch elements 52', 54' between two fingers while holding the grasping end 62 of the slide seal 42'. As shown in FIG. 10B, pressing the latch elements 52', 54' together will pivot the forward ends 52b', 54b' of the latch elements 52', 54' outward in opposite directions and allow the sealing portion 60' of the slide seal 42' to clear the forward ends 52b', 54b' allowing outward sliding movement of the slide seal 42'. The latch elements 52', 54' move against the bias applied by the spring elements 200, 202 and, when a user releases the latch elements 52', 54', they will spring back to their normally biased positions toward a latched condition as shown in FIG. 10A.

Figure 10C:
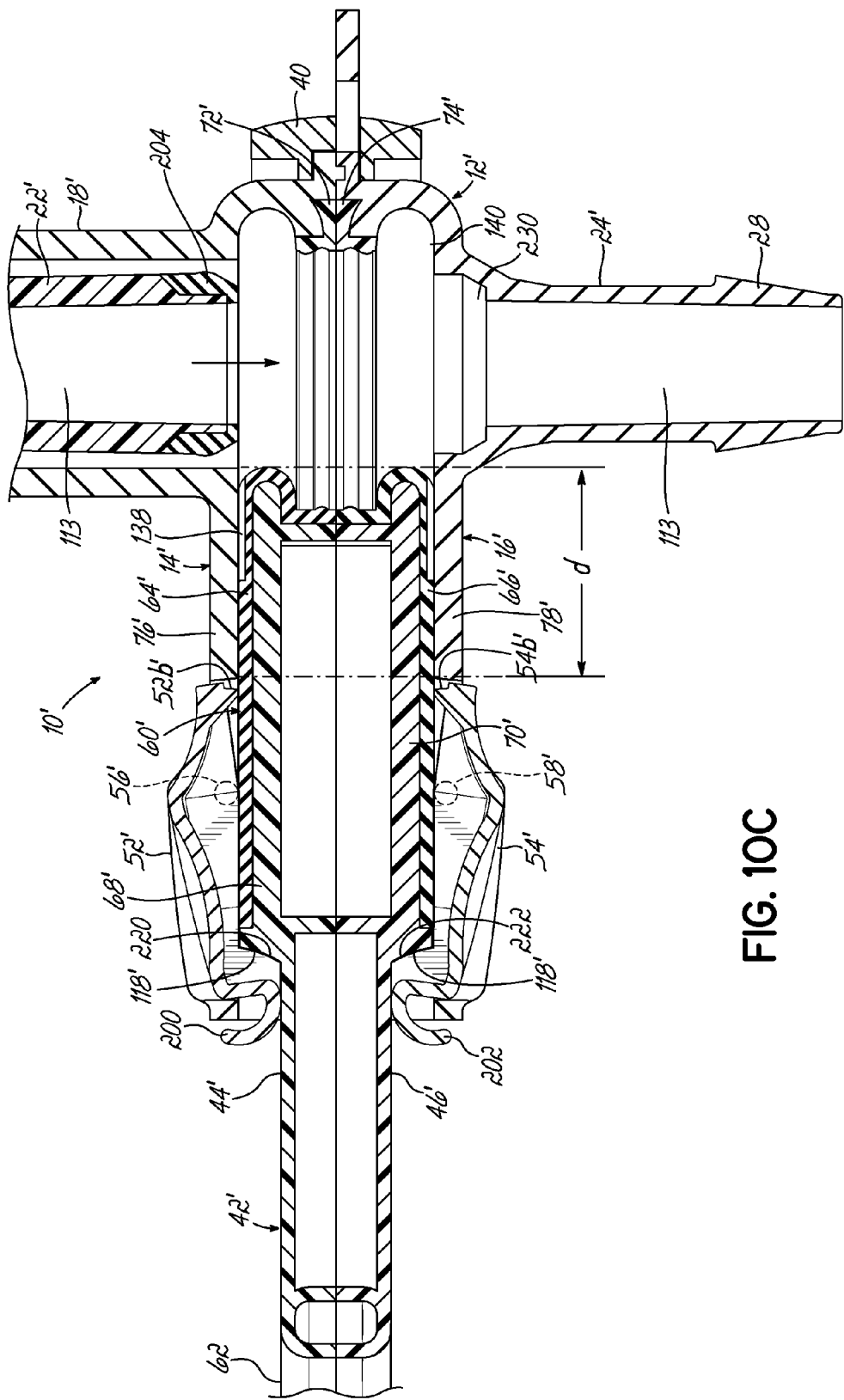
FIG. 10C is a cross sectional view similar to FIG. 10B, but illustrating the slide seal moved into its unblocking position.

As shown in the progression from FIG. 10B to FIG. 10C, with the latch elements 52', 54' biased in the manner shown, the slide seal 42' is pulled outward to its unblocking position and the rearward surface 118' of the sealing portion 60' will engage respective surfaces 220, 222 of the latch elements 52', 54' to stop the slide seal 42' at a sterile position. That is, as with the first embodiment, the sealing portion 60' stops before reaching an area of the connector 10' that may not be sterile.

Figure 10D:
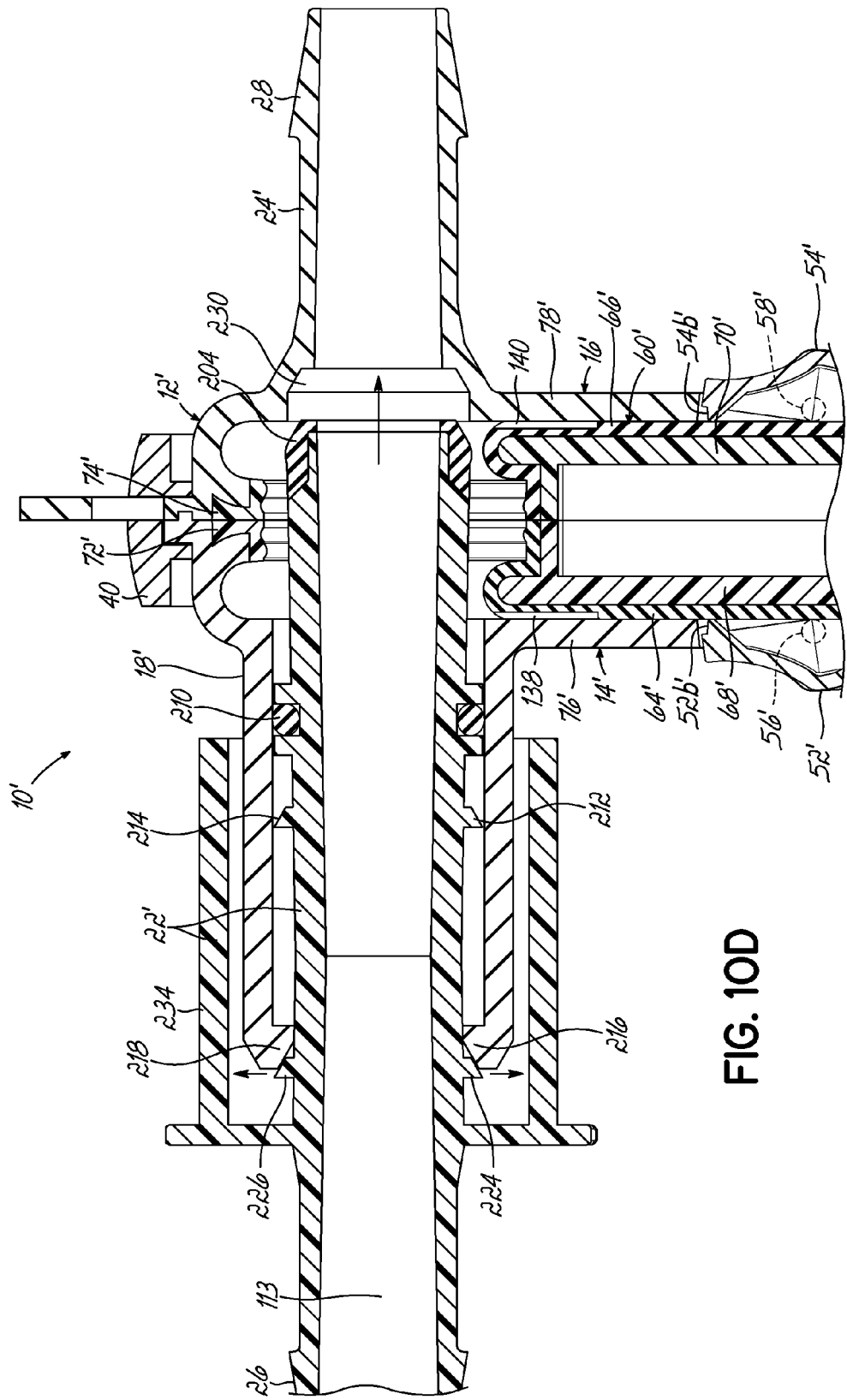
FIG. 10D is a cross sectional view similar to FIG. 10C, but illustrating a tubular fluid connector element being moved into position within the connector to establish a fluid path.
Figure 10E:
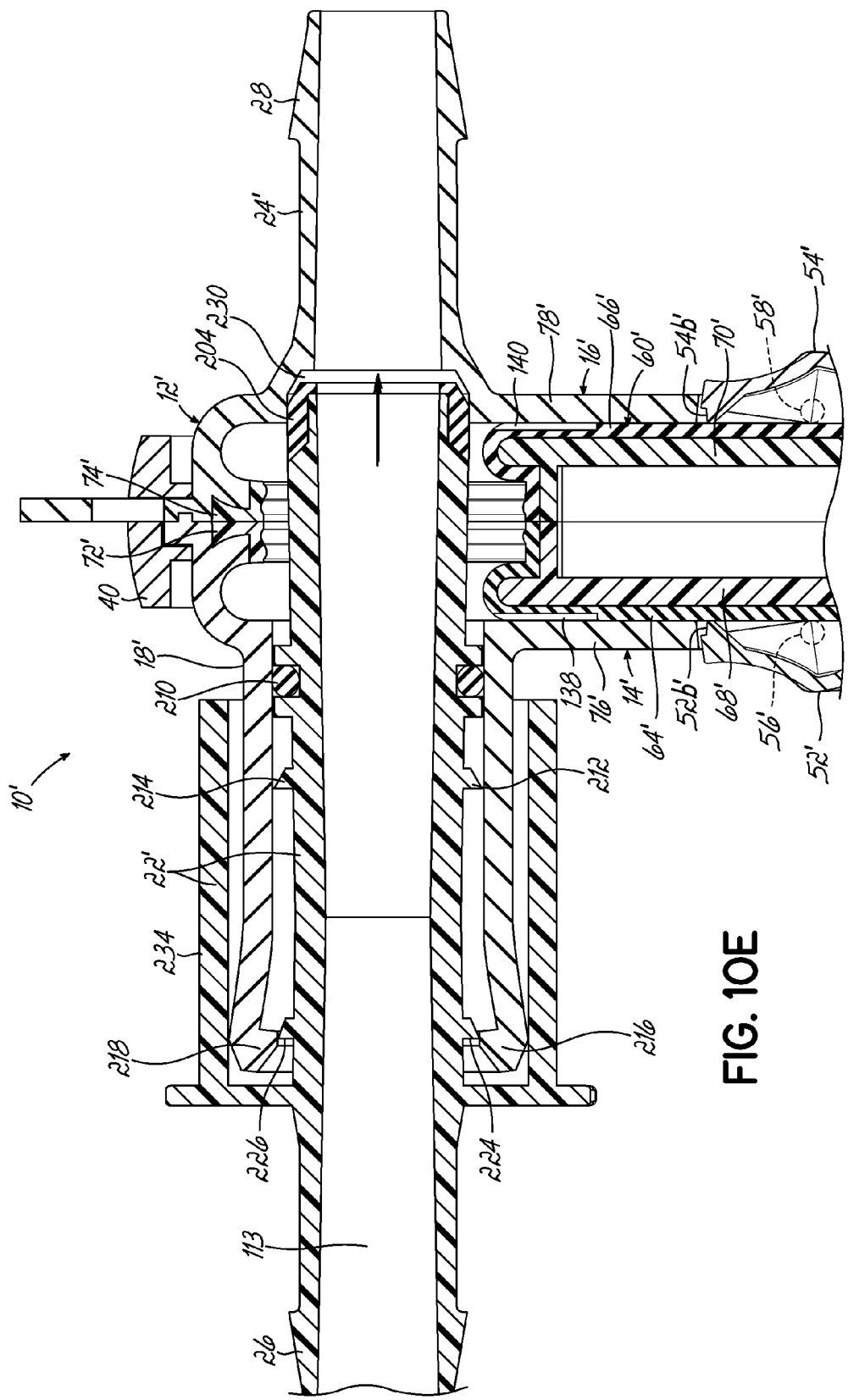
FIG. 10E is a cross sectional view similar to FIG. 10D, but illustrating further movement of the tubular fluid connector element into the housing.
Figure 10F:
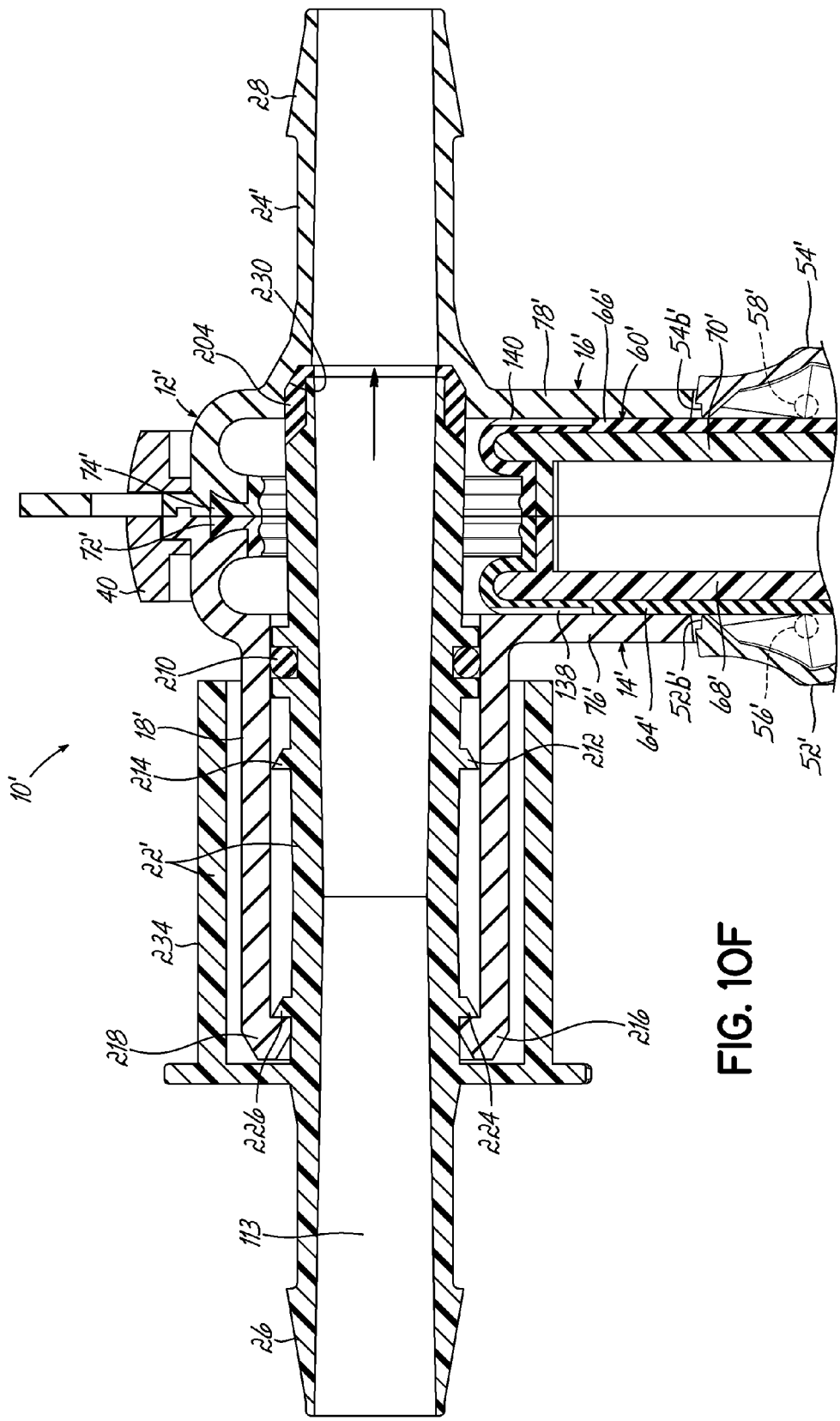
FIG. 10F is a cross sectional view similar to FIG. 10E, but illustrating complete movement of the tubular fluid connector element into a sealed position.

As shown in the progression of FIGS. 10C through 10F, the first tubular fluid connector element 22' is moved inward through the housing sections 14', 16' and the space created by the removed sealing portion 60', such that the distal end 204 which comprises an overmolded sealing rubber piece, seals against a mating circular recess 230 within the fixed tubular fluid connector element 24'. Projecting stop elements 224, 226 on the first tubular fluid connector element 22' then engage respective lips 216, 218 of the first connector port 18' to maintain the first tubular fluid connector element 22' in the sealing position shown in FIG. 10F thereby establishing the sterile fluid path 113. As shown in FIGS. 10D and 10E, a camming action between the projecting elements 224, 226 and the lips 216, 218 of the connector port 18' causes the lips 216, 218 to expand outward in a resilient manner as the projecting elements 224, 226 pass the lips 216, 218 and then snap into place as shown in FIG. 10F. It will be appreciated that the interaction and snap engagement of projecting elements 212, 214 is the same. The movement shown in the progression of FIGS. 10C-10F is a linear movement of the first tubular fluid connector element 22' into its sealed position with respect to the fixed second tubular fluid connector element 24'.

Figure 11C:
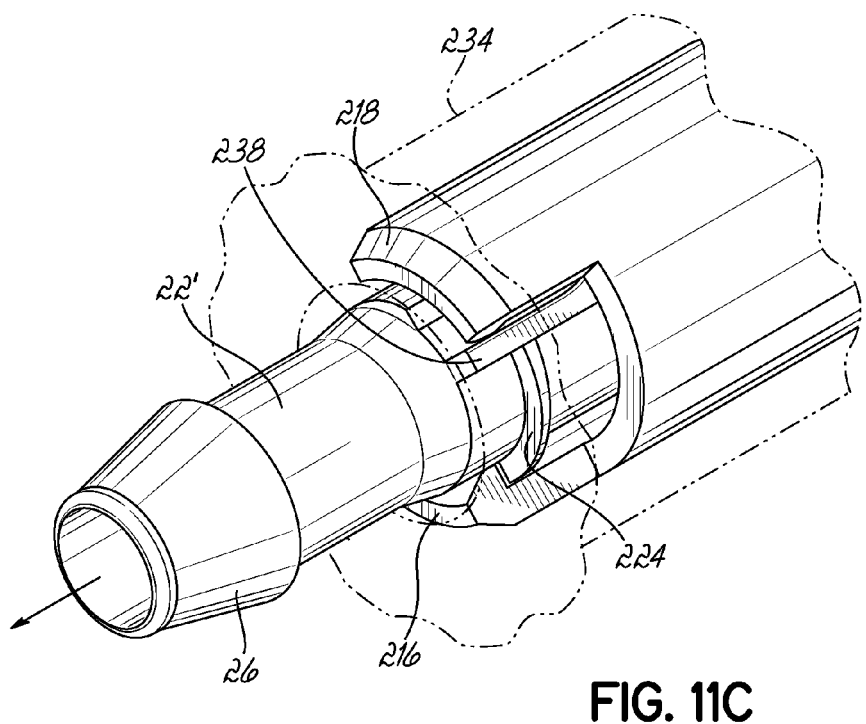
FIG. 11C is a perspective view illustrating initial withdrawing movement of the tubular fluid connector element.
Figure 11D:
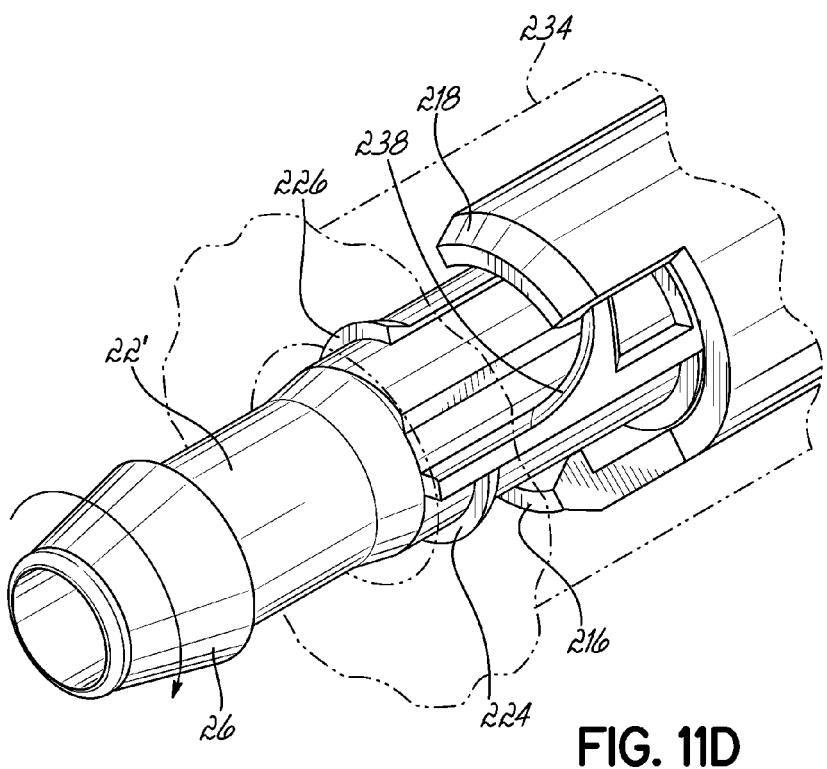
FIG. 11D is a perspective view similar to FIG. 11C but showing further withdrawing movement of the tubular fluid connector element.

If or when it is desired to move the first tubular fluid connector element 22' back to the initial position shown in FIG. 9, a rotational movement is required. This is shown in FIGS. 11A-11D. More specifically, an outer cylindrical portion 234 is integrally formed with the first tubular fluid connector element 22' and is grasped and rotated counterclockwise as shown in FIG. 11A. This rotational movement clears the projecting stop elements 224, 226 from the lips 216, 218. This allows the first tubular fluid connector element 22' to be pulled back into its initial starting position as shown in FIGS. 11B-D. As best illustrated in FIGS. 11C and 11D, the first tubular connector element 22' includes a curved track or ridge 238. A similar curved track or ridge 240 is on the opposite side. As the first fluid connector element 22' is pulled outward to the position shown in FIG. 11D, it simultaneously rotates to the initial starting position because the rear edge of lip 218 will ridge along track 238 and the rear edge of lip 216 will ridge along track 240 thereby simultaneously rotating the element 22'. In the initial starting position the projecting stop elements 212, 214 and 224, 226 will be aligned with the lips 216, 218 to allow the snap connections to be made therebetween when the first fluid connector element 22' is again pushed forward to the position shown in FIG. 9 and again as described in regard to FIGS. 10C-10F.

Figure 13:
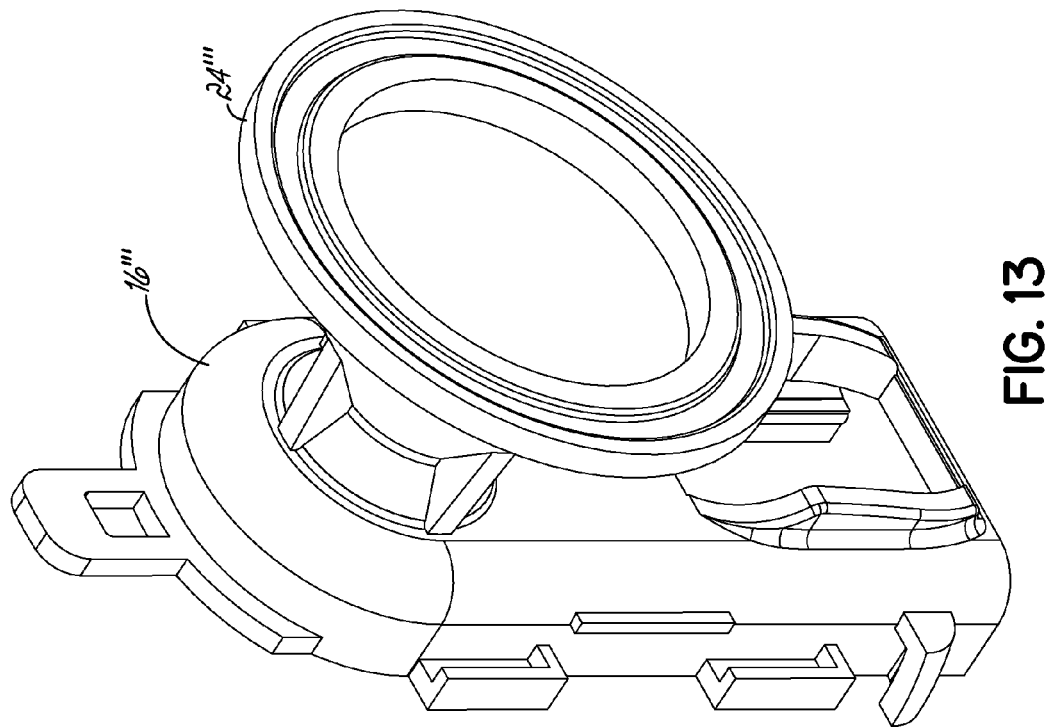
FIG. 13 is a perspective view similar to FIG. 12, but illustrating another embodiment of a fixed, tubular fluid connector element.
Figure 12:
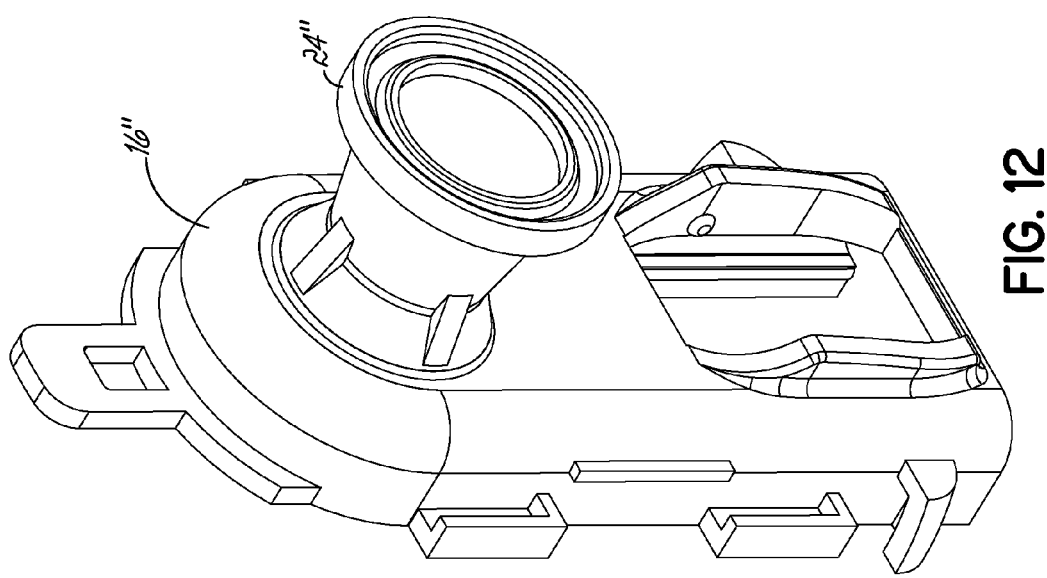
FIG. 12 is a perspective view showing a fluid connector housing section having a fixed, tubular fluid connector element similar to FIG. 7, but illustrated as an alternative design for size and/or configuration variation.
Figure 14:
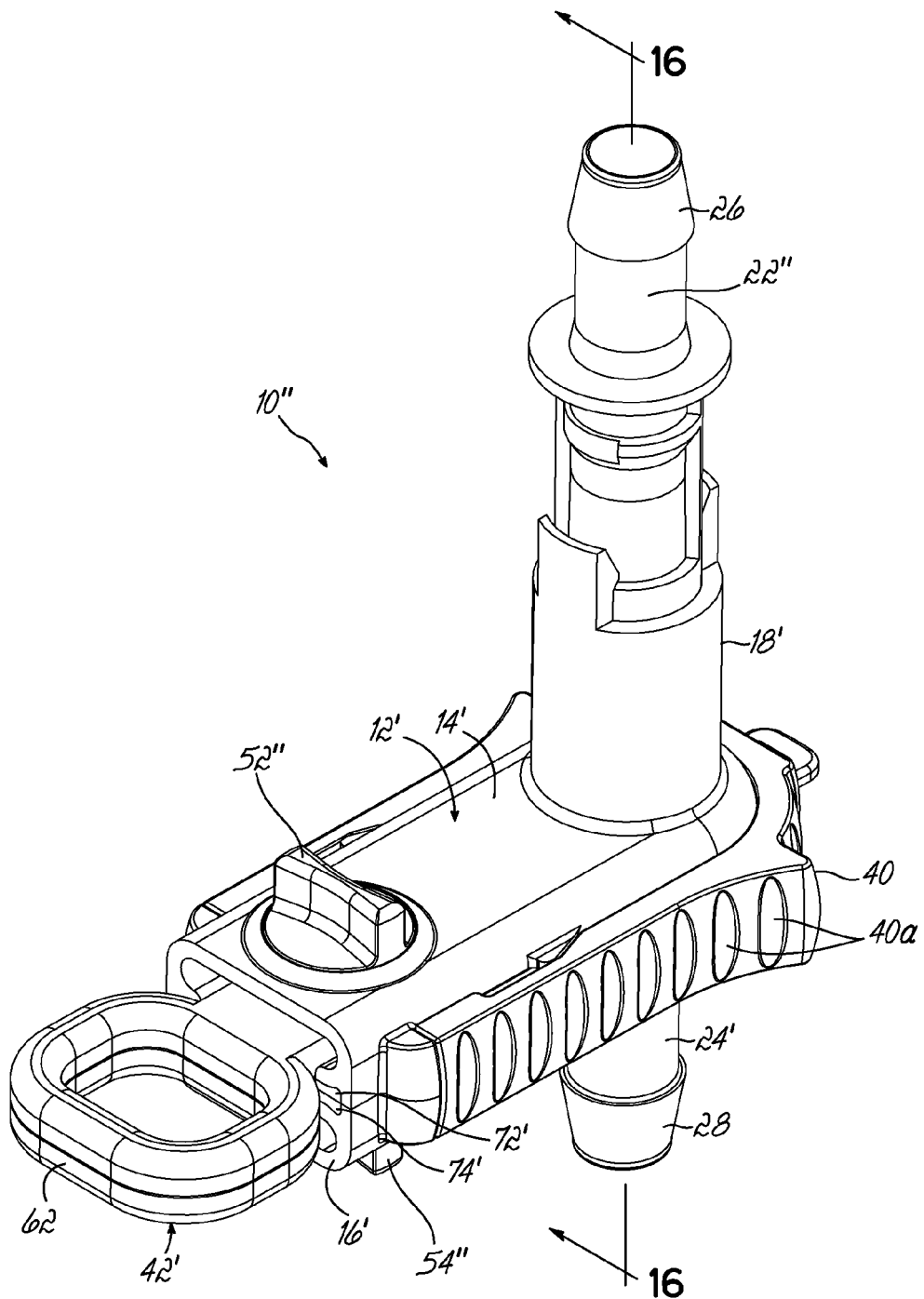
FIG. 14 is a perspective view of a fluid connector constructed in accordance with another embodiment of the invention.

FIGS. 12 and 13 illustrate alternative forms of second housing sections 16" and 16'". Specifically, FIG. 12 illustrates a first alternative of an integrally formed tubular fluid connector element 24" of a larger configuration than the integrally formed fluid connector element 24' shown in FIG. 9, for example. FIG. 13 shows a still larger integrally formed tubular fluid connector element 24'" as yet another alternative. It will be understood that various other alternative designs and configurations may be made depending on the particular application and fluid connections that are necessary.

Various components of the connector 10, 10' interact to maintain the connection sterile. In particular, this includes the interaction of the overmolded seals 64, 66, 64', 66', 72, 74 of the slide seal 42, 42' and the housing sections 14, 16, 14', 16'. The overmolded seals are designed in a fashion to not allow air or water to enter the inner portions of the connector 10, 10', thereby maintaining an hermetic seal. To this end, during use the slide seal 42, 42' is in constant contact with the housing seals 72, 74 to eliminate any air pockets or gaps before and during connection.

Prior to use, each half or section 14, 16, 14', 16' of the connector 10, 10' is separate. One half is used to attach tubing (not shown) that is also attached to a device that uses some form of fluid. The other half of the connector 10, 10' will be attached either with tubing, or some other device such as a filter as part of a fluid system. The barbs 26, 28 or any other suitable connection element may be used for these attachments. The two halves of the connector 10, 10' may be in separate locations prior to use. Each half of the connector 10, 10' is in a hermetic state with the slide seal halves 44, 46, 44', 46' respectively in the blocking positions within their respective housing sections 14, 16, 14', 16'. The flow path 113 through each housing section 14, 16, 14', 16' is therefore sealed off from the slide seal section 44, 46 or 44', 46'. Each half of the connector 10, 10' is then subjected to a sterilization process. After sterilization, the two halves of the connector 10, 10' will be joined together as described above. This connection may be made in a non-sterile environment while maintaining sterility of the flow path 113.

FIGS. 14 through 21 illustrate two additional embodiments of a fluid connector 10", 10'" constructed in accordance with various principles of the invention. In these figures, like reference numerals refer to like elements of structure with the second embodiment, described above in connection with FIGS. 7 through 11D. Therefore, these like elements will be understood to have the functions and features as discussed above and further description herein is not generally necessary. Instead, the differences between these embodiments and the second embodiment will be described in more detail below. Like reference numerals having prime ('), double prime (") or triple prime ('") marks will be understood as referring to corresponding structure of the first and/or second embodiments but having slight design differences that will be described herein and/or understood from a review of the drawings. Unless described otherwise, such elements have the same function as described for the first and/or second embodiments. Aside from the described and/or illustrated differences, the structure, function and operation of the fluid connector is as described above in connection with the first and/or second embodiments.

Figure 15:
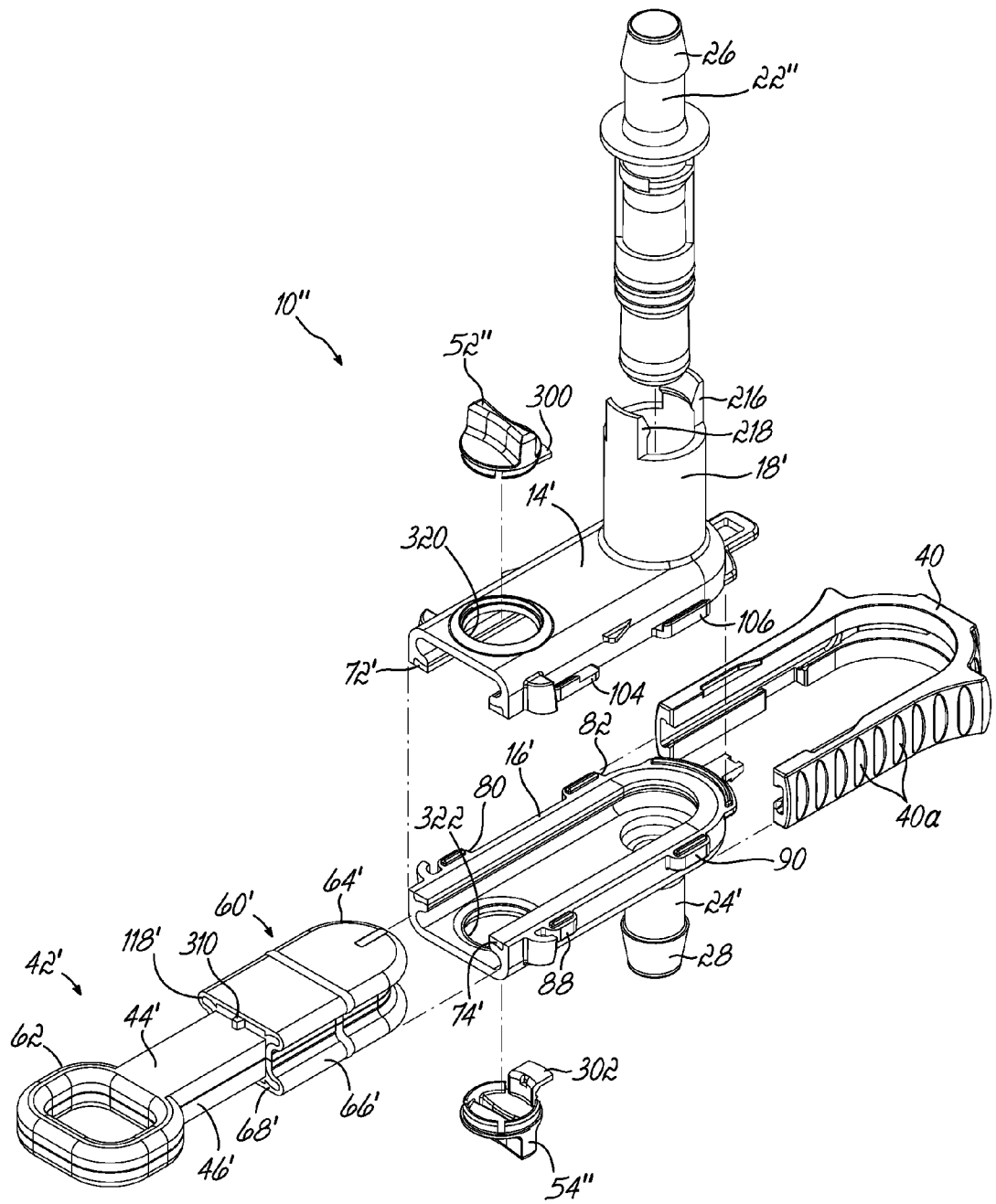
FIG. 15 is a disassembled perspective view of the fluid connector shown in FIG. 14.
Figure 16:
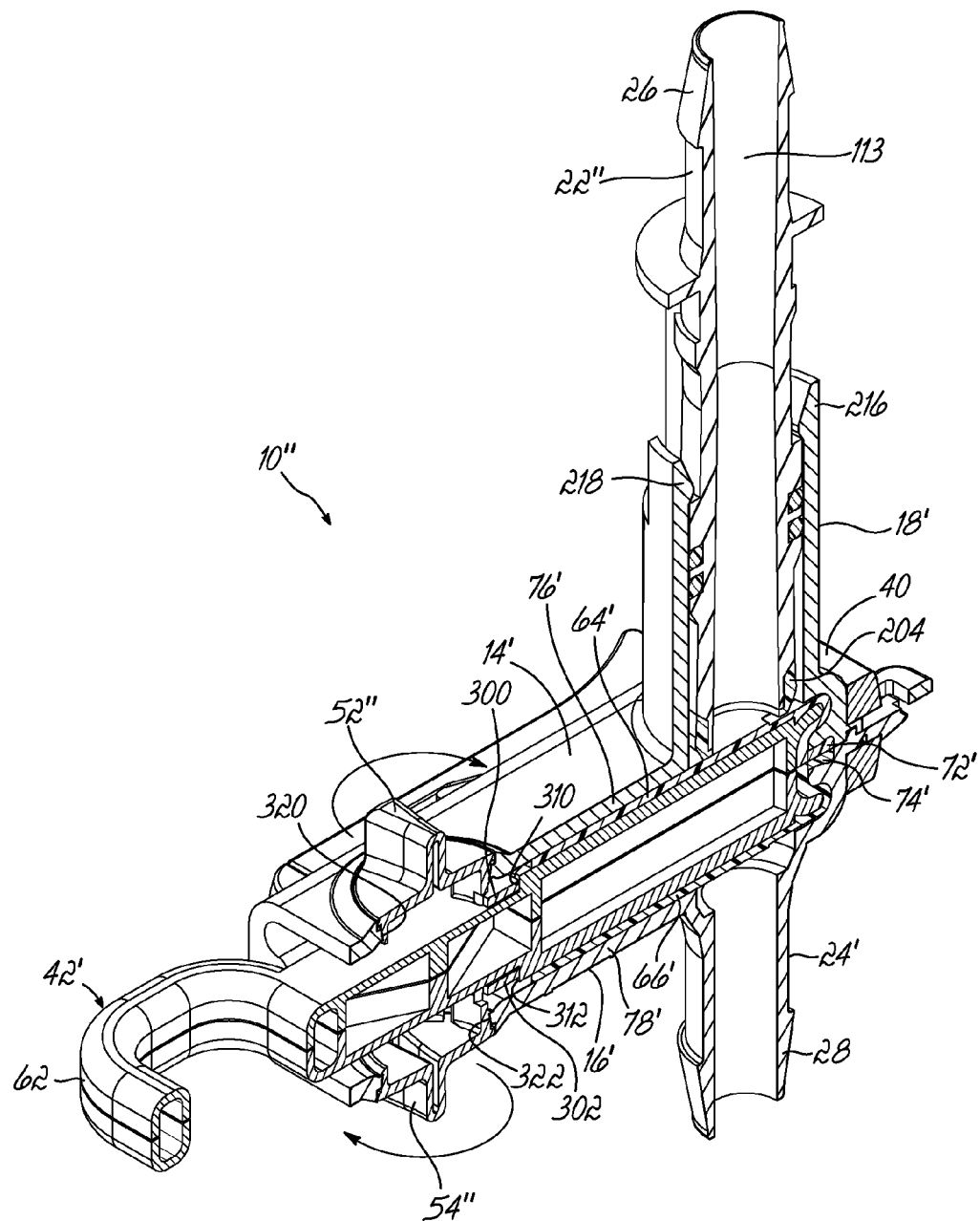
FIG. 16 is a cross sectional view taken along line 16-16 of FIG. 14 and showing an alternative latch mechanism in a locked position to prevent the slide seal from being moved outward.
Figure 17:
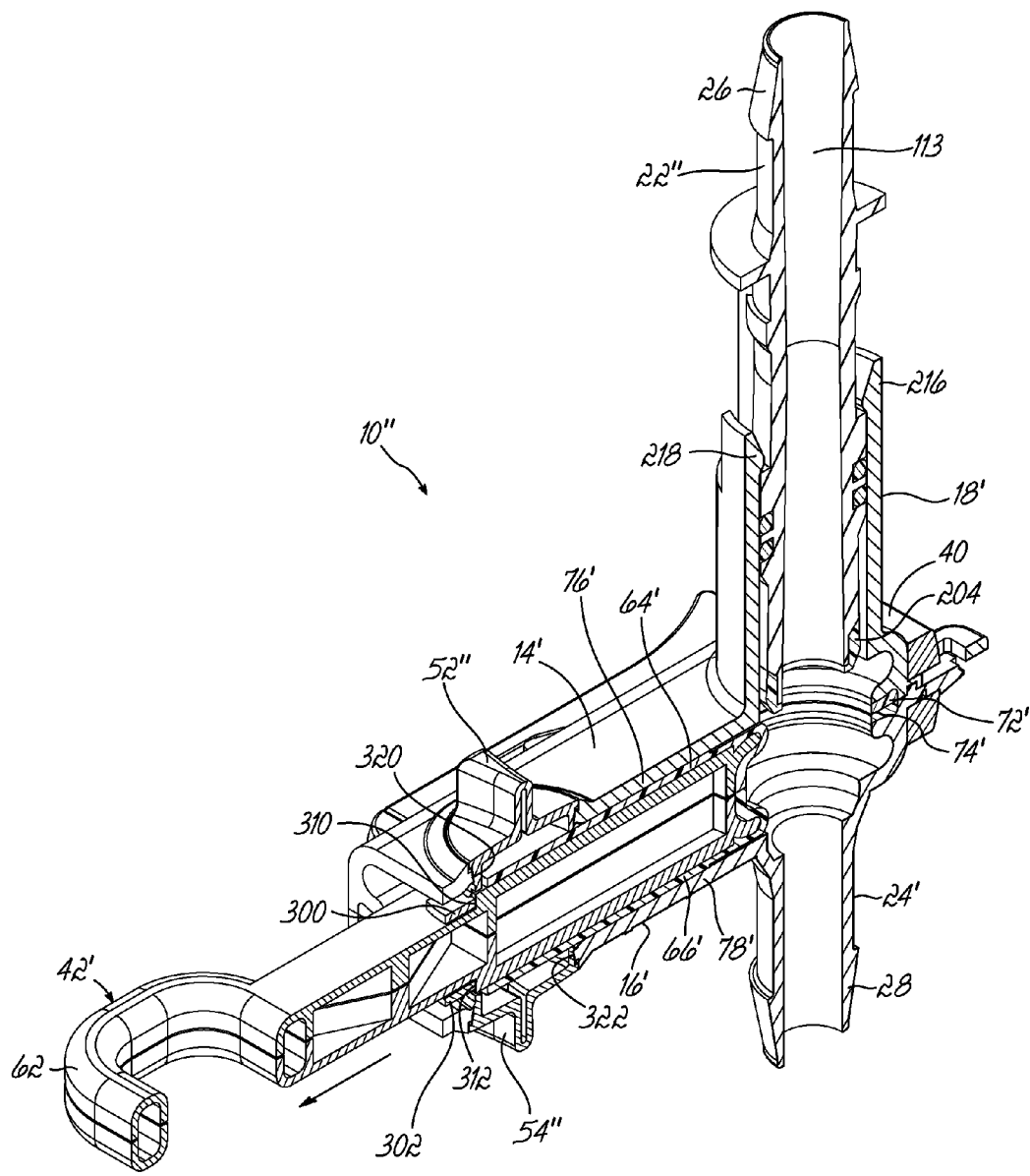
FIG. 17 is a cross sectional view similar to FIG. 16 but showing the latch mechanism in an unlocked position and the slide seal moved outward to its unblocking position.

The main difference between the embodiment shown in FIGS. 14-17 and the embodiment of FIGS. 7 through 11D relates to the latch mechanism. In this embodiment, the latch mechanism is a rotatable latch as opposed to a push button type latch previously described. As shown in FIG. 15, the latch mechanism includes a pair of latch elements 52", 54" that snap into respective apertures or holes 320, 322 when assembled to the slide seal 42' (FIGS. 14, 16 and 17) and can be independently rotated between locked positions (FIG. 16) and unlocked positions (FIG. 17). In the locked positions, the latch elements each have a stop tab 300, 302 that engages with a respective ledge 310, 312 of the slide seal 42' to prevent outward movement of the slide seal as previously described. Each latch element 52", 54" must be rotated to its unlocked position as shown in FIG. 17 in order to disengage the stop tab 300, 302 from the corresponding ledge 310, 312 and allow the slide seal 42' to be moved to its outward, unsealed position, in accordance with the method as previously described in connection with the second embodiment. As further shown in FIG. 17, the stop tabs 300, 302 provide positive stops in the unlocked position to limit the outward movement of the slide seal 42' to the unsealed position.

The other difference between the embodiment of FIGS. 14-17 and that described in connection with FIGS. 7-11D is that the cylindrical portion 234 which was integrally formed with the first tubular fluid connector element 22' has been eliminated to simplify manufacturing. Otherwise, the first tubular fluid connector element 22" shown in FIGS. 14-17 functions identically to that described in FIGS. 7-11D.

Figure 18:
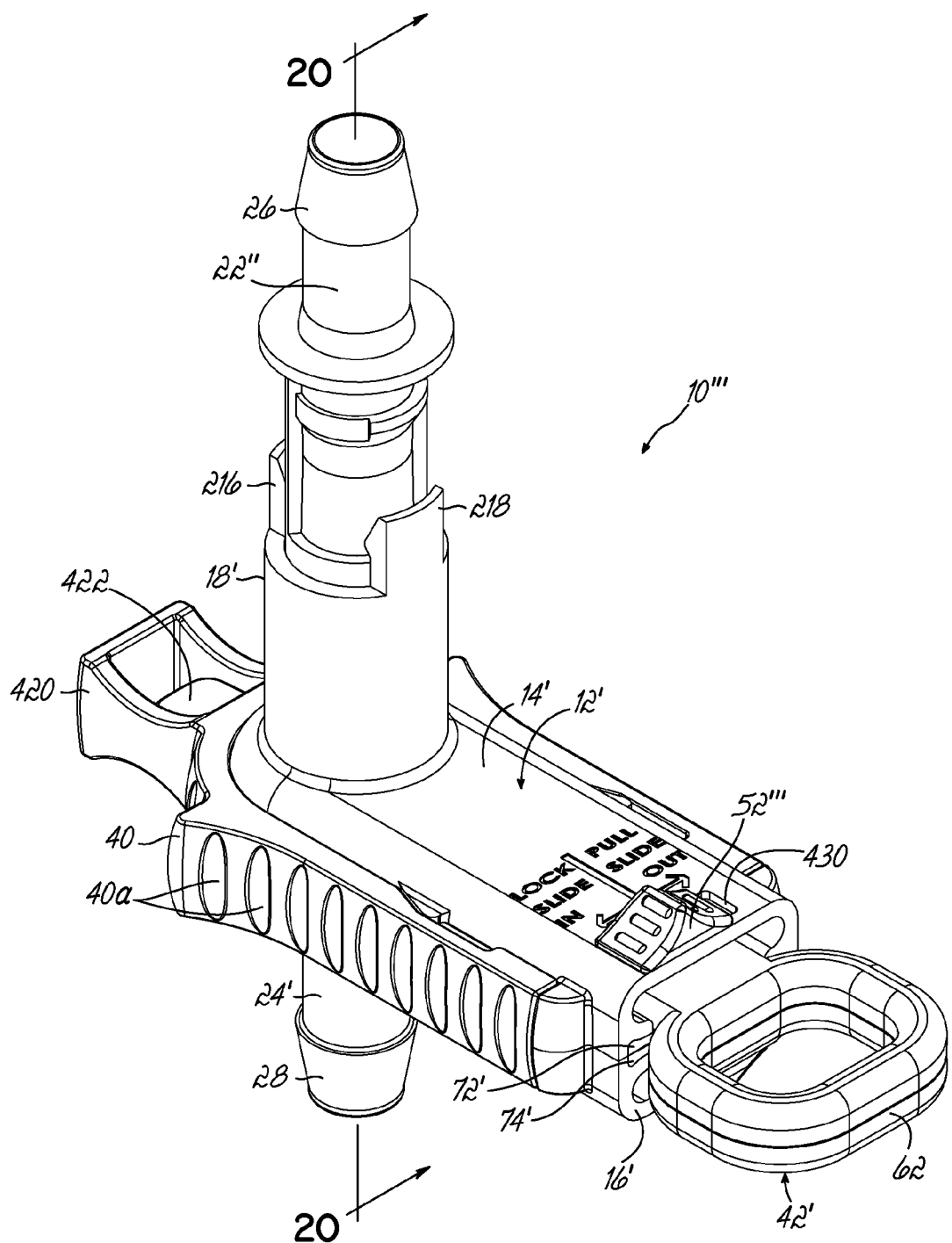
FIG. 18 is a perspective view of a fluid connector constructed in accordance with another embodiment of the invention.
Figure 19:
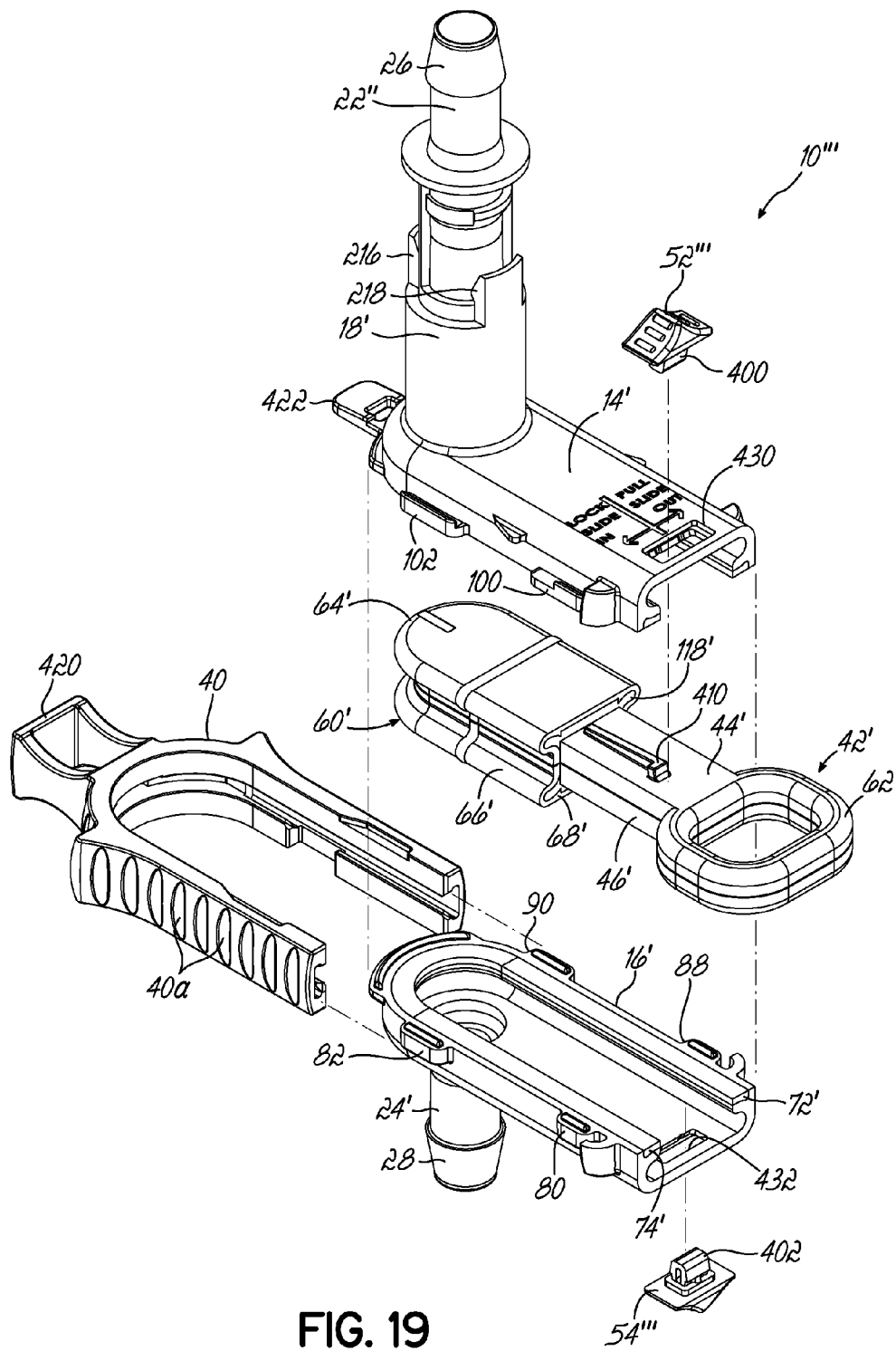
FIG. 19 is a disassembled perspective view of the fluid connector shown in FIG. 18.
Figure 20:
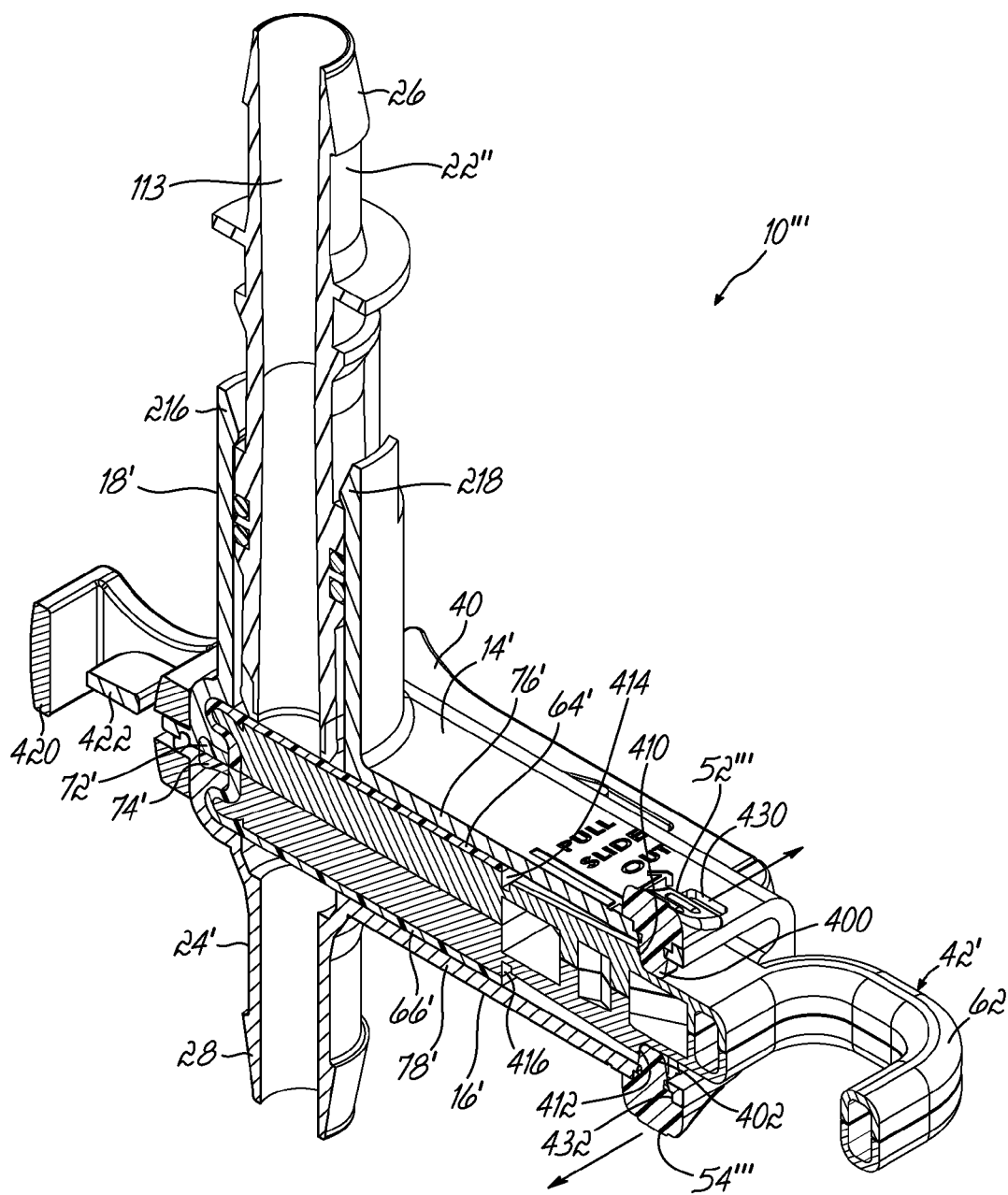
FIG. 20 is a cross sectional view taken along line 20-20 of FIG. 18 and showing an alternative latch mechanism in a locked position to prevent the slide seal from being moved outward.
Figure 21:
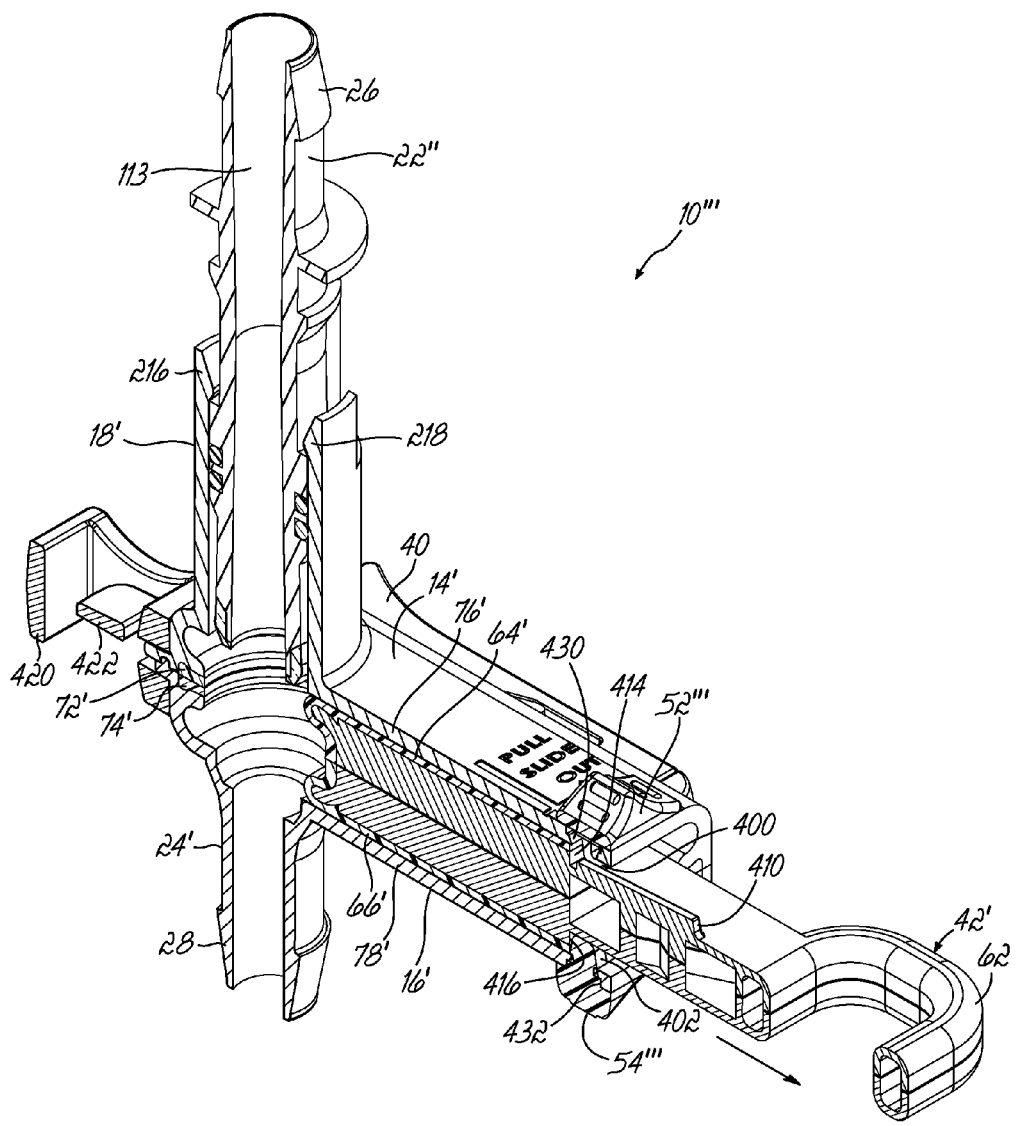
FIG. 21 is a cross sectional view similar to FIG. 20 but showing the latch mechanism in an unlocked position and the slide seal moved outward to its unblocking position.

The main difference between the embodiment of FIGS. 18-21 and the embodiment of FIGS. 7 through 11D also relates to the latch mechanism. In this embodiment, the latch mechanism is a slide latch as opposed to a push button type latch previously described as shown in FIGS. 7-11D, or a rotatable latch as shown in FIGS. 14-17. As shown in FIG. 19, the slide latch mechanism includes a pair of slide latch elements 52'", 54'" that snap into respective apertures or holes 430, 432 when assembled to the slide seal (FIGS. 18, 20 and 21) and independently slide between locked positions (FIG. 20) and unlocked positions (FIG. 21). In the locked positions, the slide latch elements 52'", 54'" each have a stop tab 400, 402 that engages with a respective first ledge 410, 412 of the slide seal to prevent outward movement of the slide seal as previously described. Each slide latch element 52'", 54'" must be slid to its unlocked position as shown in FIG. 21 in order to disengage the stop tab 400, 402 from the corresponding first ledge 410, 412 and allow the slide seal 42' to be moved to its outward, unsealed position, in accordance with the method as previously described in connection with the second embodiment. As further shown in FIG. 21, the stop tabs 400, 402 engage respective second ledges 414, 416 on the slide seal 42' to provide positive stops in the unlocked position to limit the outward movement of the slide seal 42' to the unsealed position.

The other difference between the embodiment of FIGS. 18-21 and the previous embodiments is that the slide locking element 40 includes a guard 420. A latch tab 422 is provided on the second housing section 16'. The latch tab 422 is designed to snap onto the locking element 40 to keep the locking element 40 fastened to the housing 12' when in the locked position (FIGS. 18, 20 and 21). The guard 420 acts to protect accidental release of the locking element 40. It also acts as a mechanical advantage to better allow a user to press the tab 422 and pull the locking element 40 to its unlocked or disassembled condition as previously described. Finally, the guard 420 also acts as a tamper evident opening, i.e., the user can affix a tie wrap or similar element through the opening to show the connector is ready for use.

As will be understood from a review of the description herein, connectors made in accordance with this disclosure may be disconnected and then reconnected while maintaining a sterile fluid environment during the connection and disconnection processes. For example, if desired, a sterile disconnection between housing sections may be made and then at least one of those disconnected housing sections may be re-connected in a sterile manner to another, different housing section which may or may not be of the same design as the previously connected housing section. In another example, fluid connectors 10, 10', 10" and 10'" as disclosed herein may be used in situations where the housing section 14 or 14', which includes the locking element 40 and fluid connector element 22, 22', or 22" is essentially permanently coupled to one fluid component such as a large fill tank. Another series of fluid components such as smaller tanks to be filled from the large fill tank, include the other mating portion, i.e., a housing section 16 or 16' having a fixed fluid connector element 24 or 24' Using this arrangement, only one assembly of the more complicated and expensive portion (14 or 14' and 40 and 22, 22' or 22") of the connector 10, 10', 10", or 10'" is needed for use with many of the less complicated and therefore less expensive portions (16 or 16' and 24 or 24') of the connector 10, 10', 10', or 10'".

While the present invention has been illustrated by the description of one or more embodiments thereof, and while the embodiments have been described in considerable detail, they are not intended to restrict or in any way limit the scope of the appended claims to such detail. The various features shown and described herein may be used alone or in any combination. Additional advantages and modifications will readily appear to those skilled in the art. The invention in its broader aspects is therefore not limited to the specific details, representative apparatus and method and illustrative examples shown and described. Accordingly, departures may be from such details without departing from the scope of the general inventive concept.

What is claimed is:

1. A connector adapted to form a fluid tight connection, the connector comprising:
    first and second housing sections defining a fluid path;
    a locking element configured to selectively lock said first and second housing sections together;
    a slide seal positioned between said first and second housing sections and movable between a first, blocking position in which said slide seal blocks and seals the fluid path and a second, unblocking position in which the fluid path is unblocked; and
    a latch element pivotally coupled to at least one of the first or second housing sections, the latch element being configured to selectively latch said slide seal in the first, blocking position.

2. The connector of claim 1, wherein the first and second housing sections further comprise:
    first and second fluid connector ports coupled respectively to said first and second housing sections, said first and second fluid connector ports each adapted to fluidly couple with respective first and second tubular fluid connecting elements configured to direct fluid along the fluid path.

3. The connector of claim 1, further comprising:
    a first connector port coupled to said first housing section;
    a first tubular fluid connector element configured to selectively couple with said first connector port; and
    a second tubular fluid connecting element integrally formed with said second housing section,
    said first and second tubular fluid connecting elements operative to direct fluid along the fluid path.

4. The connector of claim 1, wherein said slide seal includes a sealing portion and a grasping end opposite the sealing portion, said grasping end adapted to be grasped by a user to move the slide seal through and in fluid tight sealing engagement with the housing sections during movement between the first, blocking position and the second, unblocking position.

5. The connector of claim 4, wherein said first housing section includes a first sealing surface, and said second housing section includes a second sealing surface, said first and second sealing surfaces engaging each other in a fluid tight manner when said first and second housing sections are locked together with said locking element, and wherein said sealing portion of said slide seal further includes a sealing surface which contacts the first and second sealing surfaces when said first and second housing sections are locked together with said locking element and said slide seal is in the first, blocking position.

6. The connector of claim 1, wherein said slide seal further comprises a distal sealing tip and a proximal sealing end, and further including a stop element operative to stop said slide seal at the second, unblocking position such that distal sealing tip does not move to or past a location of the housing that is exposed to an unsealed environment.

7. The connector of claim 1, wherein said slide seal further comprises a vent for preventing vacuum from being formed in the fluid path as said slide seal is moved from the first, blocking position to the second, unblocking position.

8. The connector of claim 1, wherein said first housing section includes a first sealing surface, and said second housing section includes a second sealing surface, said first and second sealing surfaces engaging each other in a fluid tight manner when said first and second housing sections are locked together with said locking element, and wherein said slide seal further comprises a sealing surface which contacts the first and second sealing surfaces when said first and second housing sections are locked together with said locking element and said slide seal is in the first, blocking position.

9. The connector of claim 8, wherein said slide seal is formed in first and second seal sections, and a first tapered space is formed between said first and second sealing surfaces of the first and second housing sections when said first and second housing sections are locked together, and a second tapered space is formed between said first and second seal sections when said first and second housing sections are positioned adjacent to each other in an unlocked condition, and when the locking element is moved to lock said first and second housing sections together, said first and second tapered spaces are closed to thereby force fluid and/or air away from contacting locations between the first and second seal sections of the slide seal and the first and second sealing surfaces of the first and second housing sections.

10. The connector of claim 1, wherein said slide seal further comprises first and second slide seal sections, each of said first and second slide seal sections configured to be moved to the second, unblocking position in the respective first and second housing sections.

11. A connector adapted to form a fluid tight connection conditions, the connector comprising:
    first and second housing sections defining a fluid path;
    a locking collar coupled to said first and second housing sections in a sliding manner, and slidably movable between an unlocked position in which said first and second housing sections are separable, and a locked position in which said first and second housing sections are locked together in engagement with said locking collar; and
    a slide seal positioned between said first and second housing sections and movable between a first, blocking position in which said slide seal blocks and seals the fluid path and a second, unblocking position in which the fluid path is unblocked.

12. The connector of claim 11, wherein the first and second housing sections further comprise:
    first and second fluid connector ports coupled respectively to said first and second housing sections, said first and second fluid connector ports each adapted to fluidly couple with respective first and second tubular fluid connecting elements configured to direct fluid along the fluid path.

13. The connector of claim 11, further comprising:
a first connector port coupled to said first housing section;
a first tubular fluid connector element configured to selectively couple with said first connector port; and
a second tubular fluid connecting element integrally formed with said second housing section,
said first and second tubular fluid connecting elements operative to direct fluid along the fluid path.

14. The connector of claim 11, wherein said locking collar further comprises:
a U-shaped element having a closed end and an opposite, open end, and said slide seal includes a sealing portion positioned adjacent the closed end of the U-shaped element when the slide seal is in the first, blocking position, and a grasping end opposite the sealing portion and adapted to be grasped by a user to move the slide seal through the open end of the U-shaped element during movement between the first, blocking position and the second, unblocking position.

15. The connector of claim 14, wherein said first housing section includes a first sealing surface, and said second housing section includes a second sealing surface, said first and second sealing surfaces engaging each other in a fluid tight manner when said first and second housing sections are locked together with said locking collar in said locked position, and wherein said sealing portion of said slide seal further includes a sealing surface which contacts the first and second sealing surfaces when said first and second housing sections are locked together with said locking collar in the locked position and said slide seal is in the first, blocking position.

16. The connector of claim 11, wherein said slide seal further comprises a distal sealing tip and a proximal sealing end, and further including a stop element operative to stop said slide seal at the second, unblocking position such that distal sealing tip does not move to or past a location of the housing that is exposed to an unsealed environment.

17. The connector of claim 11, further comprising a latch element on at least one of the first or second housing sections and operative to selectively latch the slide seal in the first, blocking position.

18. The connector of claim 11, wherein said slide seal further comprises a vent for preventing vacuum from being formed in the fluid path as said slide seal is moved from the first, blocking position to the second, unblocking position.

19. The connector of claim 11, wherein said first housing section includes a first sealing surface, and said second housing section includes a second sealing surface, said first and second sealing surfaces engaging each other in a fluid tight manner when said first and second housing sections are locked together with said locking collar in said locked position, and wherein said slide seal further comprises a sealing surface which contacts the first and second sealing surfaces when said first and second housing sections are locked together with said locking collar in the locked position and said slide seal is in the first, blocking position.

20. The connector of claim 19, wherein said slide seal is formed in first and second seal sections, and a first tapered space is formed between said first and second sealing surfaces of the first and second housing sections when said locking collar is in the unlocked position, and a second tapered space is formed between said first and second seal sections when said locking collar is in the unlocked position, and when the locking collar is moved to the locked position said first and second tapered spaces are closed to thereby force fluid and/or air away from contacting locations between the first and second seal sections of the slide seal and the first and second sealing surfaces of the first and second housing sections.

21. The connector of claim 11, wherein said slide seal further comprises first and second slide seal sections, each of said first and second slide seal sections configured to be moved to the second, unblocking position in the respective first and second housing sections.

22. A method of making a fluid connection between first and second tubular fluid connector elements, comprising:
blocking a fluid path at a location between first and second housing sections by moving a first slide seal section to a blocking position in the first housing section and moving a second slide seal section to a blocking position in the second housing section;
locking the first and second housing sections and the first and second slide seal sections together while the first and second slide seal sections are in their blocking positions to seal the fluid path;
moving the first and second slide seal sections to an unblocking position; and
coupling the first and second tubular fluid connector elements together for fluid communication along the fluid path by moving at least one of the first or second tubular fluid connector elements with respect to the other along the fluid path.

23. The method of claim 22, wherein coupling the first and second tubular fluid connector elements further comprises:
directing the first and second tubular fluid connector elements respectively into first and second fluid connector ports of the respective first and second housing sections; and
fluidly coupling the first and second tubular fluid connector elements to each other along the fluid path.

24. The method of claim 22, wherein coupling the first and second tubular fluid connector elements further comprises:
directing the first tubular fluid connector element into a first fluid connector port of the first housing section; and
fluidly coupling the first tubular fluid connector element to a second tubular fluid connector element which is fixed to the second housing section.

25. The method of claim 22, further comprising:
sliding the first and second slide seal sections as a unitary slide seal through and in fluid tight sealing engagement with the housing sections during movement between the blocking position and the unblocking position.

26. The method of claim 25, wherein the first housing section includes a first sealing surface, and the second housing section includes a second sealing surface, and locking the first and second housing sections together further comprises:
engaging the first and second sealing surfaces with each other in a fluid tight manner as the first and second housing sections are locked together.

27. The method of claim 26, wherein the first and second slide seal sections include respective first and second sealing surfaces, and the method further comprises:
engaging the first and second sealing surfaces of the first and second slide seal sections with the first and second sealing surfaces of the respective first and second housing sections when the first and second housing sections are locked together and the first and second slide seal sections are in their blocking positions.

28. The method of claim 27, further comprising:
forming a first tapered space between the first and second sealing surfaces of the first and second housing sections;
forming a second tapered space between the first and second sealing surfaces of the first and second seal sections; and
closing the first and second tapered spaces as the first and second housing sections are locked together to thereby force fluid and/or air away from contacting locations between the first and second sealing surfaces of the first and second slide seal sections and the first and second sealing surfaces of the first and second housing sections.

29. The method of claim 22, wherein the first and second slide seal sections further comprise a unitary slide seal when the first and second housing sections are locked together, the slide seal having a distal sealing tip and a proximal sealing end, and the method further comprises:
stopping the slide seal at the unblocking position using a stop element such that distal sealing tip does not move to or past a location of first and second sealing surfaces that is exposed to an unsealed environment.

30. The method of claim 22, wherein the first and second slide seal sections further comprise a unitary slide seal when the first and second housing sections are locked together, and the method further comprises:
using a latch element on at least one of the first or second housing sections to selectively latch the slide seal in the blocking position.

31. The method of claim 22, wherein the first and second slide seal sections further comprise a unitary slide seal when the first and second housing sections are locked together, and the method further comprises:
venting the fluid path through a vent path in the slide seal as the slide seal is moved to the unblocking position.

* * * * *